(12) United States Patent
Duatti et al.

(10) Patent No.: US 7,445,765 B2
(45) Date of Patent: Nov. 4, 2008

(54) RADIOPHARMACEUTICAL FOR DIAGNOSTIC IMAGING CONTAINING A TECHNETIUM-99M NITRIDE HETEROCOMPLEX

(75) Inventors: Adriano Duatti, Ferrara (IT); Cristina Bolzati, Ferrara (IT); Licia Uccelli, Ferrara (IT); Alessandra Boschi, Bologna (IT); Fiorenzo Refosco, Vicenza (IT); Francesco Tisato, Padua (IT)

(73) Assignee: Nihon Medi-Physics Co., Ltd., Tokyo (JP)

( * ) Notice: Subject to any disclaimer, the term of this patent is extended or adjusted under 35 U.S.C. 154(b) by 504 days.

(21) Appl. No.: 10/332,707

(22) PCT Filed: Jul. 25, 2001

(86) PCT No.: PCT/JP01/06402

§ 371 (c)(1),
(2), (4) Date: Sep. 4, 2003

(87) PCT Pub. No.: WO02/09771

PCT Pub. Date: Feb. 7, 2002

(65) Prior Publication Data

US 2004/0018147 A1    Jan. 29, 2004

(30) Foreign Application Priority Data

Jul. 28, 2000    (JP) .............................. 2000-228898

(51) Int. Cl.
*A61K 49/00*    (2006.01)
(52) U.S. Cl. ....................................... 424/9.1
(58) Field of Classification Search ................... 424/9.1
See application file for complete search history.

(56) References Cited

U.S. PATENT DOCUMENTS 5,162,534 A * 11/1992 Lee et al. ................. 546/269.7
5,288,476 A    2/1994 Pasqualini et al.
5,300,278 A    4/1994 Pasqualini et al.
5,399,339 A * 3/1995 Pasqualini et al. ......... 424/1.53
5,496,929 A    3/1996 Pasqualini et al.
6,270,745 B1 * 8/2001 Duatti et al. ............... 424/1.77

FOREIGN PATENT DOCUMENTS

| EP | 0949265 | * 12/1997 |
| EP | 0 949 265 | 10/1999 |
| EP | 0 949 265 A1 | 10/1999 |
| WO | WO 89/08657 | 9/1989 |
| WO | WO 90/06137 | 6/1990 |
| WO | WO 92/00982 | 1/1992 |
| WO | WO 93/01839 | 2/1993 |
| WO | WO 98/27100 A1 | 6/1998 |

OTHER PUBLICATIONS

Pasqualini, R. Bis(dithiocarbamato)nitrido technetium-9m radiopharmaceuticals: A class of neutral myocardial imaging agents J. Nucl. Med. 1994, 35, 334-341.*
Pasqualini et al. J. Nucl. Med. 1994, 35, 334-341.*
Cristina Bolzati, et al, Geometrically Controlled Selective Formation of Nitrido Technetium(V) Asymmetrical Heterocomplexes with Bidentate Ligands, *J. Am. Chem. Soc.*, May 2000, V122, No. 18 pp. 4510-4511.

* cited by examiner

*Primary Examiner*—Michael G. Hartley
*Assistant Examiner*—Melissa Perreira
(74) *Attorney, Agent, or Firm*—Sughrue Mion, PLLC

(57) ABSTRACT

A radiopharmaceutical for diagnostic imaging containing as an active ingredient a technetium-99m nitride heterocomplex comprising technetium-99m nitride and two different ligands coordinated therewith, i.e., a bisphosphinoamine compound as a π electron acceptor and a bidentate ligand as a π electron donor and represented by the following formula (I): $[^{99m}Tc(N)(PNP)(XY)]^+$ (I) wherein $^{99m}Tc(N)$ is technetium-99m nitride, PNP is a bisphosphinoamine compound and XY is a bidentate ligand, is markedly accumulated in heart and adrenal glands and hence is useful for radiodiagnostic imaging of heart and adrenal glands.

5 Claims, No Drawings

RADIOPHARMACEUTICAL FOR DIAGNOSTIC IMAGING CONTAINING A TECHNETIUM-99M NITRIDE HETEROCOMPLEX

TECHNICAL FIELD

The present invention relates to a radiopharmaceutical for diagnostic imaging containing a technetium-99m nitride heterocomplex as an active ingredient. More particularly, the present invention relates to a radiopharmaceutical for diagnostic imaging which contains as an active ingredient a technetium-99m nitride heterocomplex comprising technetium-99m nitride and two different ligands coordinated therewith, i.e., a diphosphine compound as a π eletron acceptor and a bidentate ligand as a π electron donor, and is suitable especially for radiodiagnostic imaging of heart and adrenal glands.

BACKGROUND ART

Of radioactive transition metals used in radiopharmaceuticals, Tc-99m is a nuclide most often used in the field of radiodiagnostic imaging because it is advantageous, for example, in that since the energy of γ-rays emitted by Tc-99m is 141 keV and the half-life of Tc-99m is 6 hours, Tc-99m is suitable for imaging, and that Tc-99m can easily be obtained by means of a $^{99}$Mo—$^{99m}$Tc generator. It is considered that if a physiologically active substance or the like can be attached to this nuclide without impairing the activity, the resulting compound is useful as a diagnostic agent or a therapeutic agent.

The attempts described below were made to achieve such attachment. Transition metal nitride complexes are excellent in stability to hydrolysis. Therefore, when a transition metal nitride complex is subjected to exchange reaction with any of various ligands having a useful physiological activity, when used in a pharmaceutical, the nitride group of the nitride complex can remain bonded strongly to the metal atom. Accordingly, technetium nitride complexes having various substituents have been proposed. For example, WO 90/06137 discloses diethyl bisdithiocarbamate-Tc nitride complex, dimethyl bisdithiocarbamate-Tc nitride complex, di-n-propyl bisdithiocarbamate-Tc nitride complex, N-ethyl-N-(2-ethoxyethyl) bisdithiocarbamate-Tc nitride complex, etc. In addition, WO 89/08657, WO 92/00982, WO 93/01839 and the like disclose processes for producing a technetium nitride complex which comprises reacting a polyphosphine or the like as a reducing agent for technetium with technetium oxide, then reacting a nitride of a metal or ammonium as a nitrogen source for nitride with the reaction product to convert it to the corresponding nitride, and then coordinating a physiologically active monoclonal antibody or the like with this nitride.

In these processes, the choice of the physiologically active ligand is so important that it determines properties of the resulting pharmaceutical. But, the metal nitride complex can have various numbers of coordination positions from monodentate to tetradentate and hence is formed in plural forms. Therefore, it has been difficult to obtain a single complex stoichiometrically having a specific physiologically active ligand.

WO 98/27100 discloses that when a disphosphine compound is coordinated at two of the four coordination positions of technetium-99m nitride and a bidentate ligand having an electron-donating atom pair is coordinated at the remaining two coordination positions, the bidentate ligand is stoichiometrically coordinated, so that a single technetium-99m nitride heterocomplex can be stably obtained. However, no technetium-99m nitride heterocomplex formed by coordination of a specific bidentate ligand having a useful physiological activity has yet been obtained. Furthermore, no technetium-99m nitride heterocomplex has yet been obtained which is accumulated in specific organs, in particular, heart and adrenal glands and is accumulated in these organs in a higher proportion than in other organs, resulting in a clear distinction between an image obtained and a background.

DISCLOSURE OF INVENTION

In view of such conditions, the present invention is intended to provide a radiopharmaceutical for diagnostic imaging comprising a technetium-99m nitride heterocomplex which is markedly accumulated in specific organs, in particular, heart and adrenal glands and hence is useful for radiodiagnostic imaging.

That is, the present invention is a radiopharmaceutical for diagnostic imaging comprising as an active ingredient a technetium-99m nitride heterocomplex comprising technetium-99m nitride and two different ligands coordinated therewith, i.e., a diphosphine compound as a π electron acceptor and a bidentate ligand as a π electron donor and represented by the following formula (1):

wherein $^{99m}$Tc(N) is technetium-99m nitride, PNP is a bisphosphinoamine compound and XY is a bidentate ligand.

Said bisphosphinoamine compound is preferably a compound represented by the following formula (2):

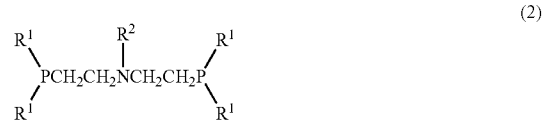

wherein $R^1$ is an alkyl group, a phenyl group or a group represented by the following formula (3):

wherein 1 is an integer in a range of $1 \leq 1 \leq 4$ and 1' is an integer in a range of $0 \leq 1' \leq 3$; and $R^2$ is a hydrogen atom, an alkyl group, a substituted alkyl group, an aryl group, a substituted aryl group, an amino group, an amino acid chain, a biologically active group, a group represented by the formula (3) as defined above or a group represented by —C(═O)R' wherein R' is a hydrogen atom, an alkyl group, a substituted alkyl group, an aryl group, a substituted aryl group, an amino group, an amino acid chain or a biologically active group.

Said bidentate ligand is preferably dithiocarbamic acid, a derivative thereof, dithiocarbazic acid or derivative thereof, which is represented by the following formula (4):

wherein $R^3$ is a hydrogen atom, alkaline metal, a positive monocation or the corresponding salt, and alkyl group, and $R^4$ and $R^5$ are independently a hydrogen atom, amino group, alkyl group, substituted alkyl group, branched alkyl group or alkoxy group, 2-aminoethanethiol, derivatives thereof, which are represented by the following formula (5):

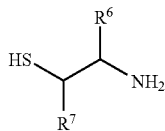
(5)

wherein $R^6$ and $R^7$ are independently a hydrogen atom, an alkyl group or an aryl group, and 2-aminopropanethiol, derivatives thereof, which are represented by the following formula (6):

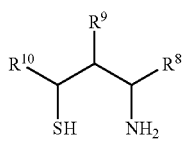
(6)

wherein $R^8$, $R^9$, $R^{10}$ are independently a hydrogen atom, an alkyl group or an aryl group.

In the above formula (4), $R^3$ is preferably a hydrogen atom, an alkyl group, an alkaline metal, a positive monocation or the corresponding salt, $R^4$ and $R^5$ are independently an alkyl group of 1 to 9 carbon atoms, a substituted alkyl group which are represented by the following formula (7), (8), (9) or (10):

$$—(CH_2)_m O(CH_2)_{m'} CH_3 \quad (7)$$

wherein m is an integer in a range of $1 \leq m \leq 8$ and m' is an integer in a range of $0 \leq m' \leq 8$,

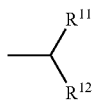
(8)

wherein $R^{11}$, $R^{12}$ are independently an alkyl group or an aryl group,

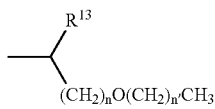
(9)

wherein $R^{13}$ is an alkyl group or an aryl group, n and n' are independently an integer in a range of $0 \leq n \leq 4$, $0 \leq n' \leq 4$,

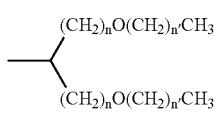
(10)

wherein n and n' are independently an integer in a range of $0 \leq n \leq 4$, $0 \leq n' \leq 4$.

BEST MODE FOR CARRYING OUT THE INVENTION

The technetium-99m nitride heterocomplex according to the present invention, i.e., the technetium-99m nitride heterocomplex comprising technetium-99m nitride and two different ligands coordinated therewith, i.e., a bisphosphinoamine compound as a π eletron acceptor and a bidentate ligand as a π electron donor can be represented by the following formula (1):

wherein $^{99m}Tc(N)$ is technetium-99m nitride, PNP is a bisphosphinoamine compound as a π electron acceptor and XY is a bidentate ligand as a π electron donor. In the formation process of the technetium-99m nitride heterocomplex, a fragment $[^{99m}Tc(N) (PNP)]^{2+}$ formed by coordination of the bisphosphinoamine compound (hereinafter properly abbreviated as PNP) has a high electrophilicity, and the bidentate ligand XY is coordinated with this fragment selectively and quantitatively to form the monocationic asymmetric technetium-99m nitride heterocomplex $[^{99m}Tc(N) (PNP) (XY)]^+$.

In general, a diphosphine compound, a π electron acceptor is used as one of the two different ligands of the technetium-99m nitride heterocomplex of the above formula (1). In the present invention, the diphosphine compound is preferably a compound of the above formula (2). The bidentate ligand XY is preferably dithiocarbamic acid, dithiocarbazic acid, or a derivative thereof, which are represented by the above formula (4), 2-aminoethnethiol or a derivative thereof which represented by the above formula (5), 3-aminopropanethiol or a derivative thereof which represented by the above formula (6).

Dithiocarbamic acid, dithiocarbazic acid, or a derivative thereof has a sulfur atom pair [S, S] as an electron-donating atom pair, also 2-aminoethnethiol or a derivative thereof or 3-aminopropanethiol or a derivative thereof has an electron-donating atom pair [N, H]. The technetium-99m nitride heterocomplex formed by coordination of such two different ligands PNP and XY is stable monocationic complex having a high fat-solubility (see Table 1 given hereinafter). Such complex is stable for imaging organs, in particular, heart and adrenal glands because it is accumlated in specific organs, in particular, heart and adrenal glands and is ahese accumulated in these organs in a higher proportion than other organs, rsulting in a clear ditribution between an image obtained anda background.

Specific examples of the bisphosphinoamine compound PNP of the above formula (2) are bis(diphenylphosphinoethyl)amine, bis(diphenylphosphinoethyl)ethylamine, bis(diphenylphosphinoethyl)propylamine, bis(diphenylphosphinoethyl)methoxyethylamine, bis(diphenylphosphinoethyl)butylamine, bis(diphenylphosphinoethyl)acetonylamine, bis(dimethoxyphosphinoethyl)amine, bis(dimethoxyphosphinoethyl)methylamine, bis(dimethoxyphosphinoethyl)ethylamine, bis(dimethoxyphosphinoethyl)propylamine, bis(dimethoxypropylphosphinoethyl)ethylamine, bis(dimethoxypropylphosphinoethyl)propylamine, bis(dimethoxypropylphosphinoethyl)methoxyethylamine, bis(dimethoxypropylphosphinoethyl)ethoxyethylamine, bis(diethoxypropylphosphinoethyl)ethoxyethylamine, bis(diethoxyethylphosphinoethyl)ethylamine, bis(diethoxyethylphosphinoethyl)propylamine, bis(diethoxyethylphosphinoethyl)methoxyethylamine, bis(dimethylphosphinoethyl)methylamine, bis(dipropoxymethylphosphinoethyl)ethoxyethylamine, etc.

There are preferably used bis(dimethoxypropylphosphinoethyl)methoxyethylamine, bis(diethoxyethylphosphinoethyl)ethylamine, bis(diethoxyethylphosphinoethyl)propylamine, bis(dimethoxypropylphosphinoethyl)ethoxyethylamine, bis(diethoxypropylphosphinoethyl)ethoxyethylamine, bis(diethoxyethylphosphinoethyl)methoxyethylamine, bis(dimethylphosphinoethyl)methylamine, bis(dipropoxymethylphosphinoethyl)ethoxyethylamine, etc. Bis(dimethoxypropylphosphinoethyl)methoxyethylamine, bis(dimethoxylpropylphosphinoethyl)ethoxyethylamine and bis(diethoxypropylphosphinoethyl)ethoxyethylamine are especially preferable.

Preferable specific examples of the bidentate ligand XY of the above formula (4) are N-methyl-S-methyl dithiocarbazate, N-dimethyl dithiocarbamate, N-diethyl dithiocarbamate, N-dipropyl dithiocarbamate, N-methoxy-N-methyl dithiocarbamate, N-methoxyethyl-N-ethyl dithiocarbamate, N-methoxypropyl-N-ethyl dithiocarbamate, N-methoxyethyl-N-butyl dithiocarbamate, N-dimethoxyethyl dithiocarbamate, N-diethoxyethyl dithiocarbamate, N-diethoxypropyl dithiocarbamate, N-diethoxybutyl dithiocarbamate, N-dipropoxyethyl dithiocarbamate, N-dibutoxyethyl dithiocarbamate, N-dimethoxypropyl dithiocarbamate, N-dimethoxyisopropyl dithiocarbamate, N-ethoxy-N-ethyl dithiocarbamate, N-ethoxypropyl-N-propyl dithiocarbamate, N-methoxyethyl-N-isopropyl dithiocarbamate, N-ethoxyethyl-N-propyl dithiocarbamate, N-ethoxyethyl-N-ethyl dithiocarbamate, N-propoxy-N-ethyl dithiocarbamate, etc. Of these, especially preferable are N-dimethyl dithiocarbamate, N-diethyl dithiocarbamate, N-dipropyl dithiocarbamate, N-methoxy-N-methyl dithiocarbamate, N-ethoxy-N-ethyl dithiocarbamate, N-methoxyethyl-N-ethyl dithiocarbamate, N-ethoxyethyl-N-isopropyl dithiocarbamate, N-ethoxyethyl-N-ethyl dithiocarbamate, N-methoxypropyl-N-ethyl dithiocarbamate, N-dimethoxyethyl dithiocarbamate and N-diethoxyethyl dithiocarbamate.

In the present invention, the radiopharmaceutical for diagnostic imaging is especially preferably one in which the bisphosphinoamine compound PNP is selected from the group consisting of bis(dimethoxypropylphosphinoethyl)methoxyethylamine, bis(dimethoxypropylphosphinoethyl)ethoxyethylamine and bis(diethoxypropylphosphinoethyl)ethoxyethylamine, and the bidentate ligand XY is selected from the group consisting of N-dimethyl dithiocarbamate, N-diethyl dithiocarbamate, N-dipropyl dithiocarbamate, N-methoxy-N-methyl dithiocarbamate, N-ethoxy-N-ethyl dithiocarbamate, N-methoxyethyl-N-ethyl dithiocarbamate, N-ethoxyethyl-N-isopropyl dithiocarbamate, N-ethoxyethyl-N-ethyl dithiocarbamate, N-methoxypropyl-N-ethyl dithiocarbamate, N-dimethoxyethyl dithiocarbamate and N-diethoxyethyl dithiocarbamate.

Tables 3 to 18 given hereinafter show the biodistribution in rats of each of technetium-99m nitride heterocomplexes obtained by using bis(dimethoxypropylphosphinoethyl)methoxyethylamine (PNP3), bis(dimethoxypropylphosphinoethyl)-ethoxyethylamine (PNP5) or bis(diethoxypropylphosphinoethyl)ethoxyethylamine (PNP6) as the bisphosphinoamine compound PNP and each of various bidentate ligands as the bidentate ligand XY. Tables 19 and 20 show, for comparison, data on the biodistribution in rats of each of a technetium-99m complex of hexakis(2-methoxyisobutylisonitrile) (hereinafter abbreviated as ($^{99m}$Tc) (MIBI)) and a technetium-99m complex of bis[bis(2-ethoxyethyl)phosphino]ethane-(tetrofosmin) (hereinafter abbreviated as ($^{99m}$Tc) (Tf)) which are technetium-99m complexes different in kind from those according to the present invention. Tables 21 to 23 given hereinafter show data showing the variations with time of heart accumulation, heart/lung ratios and heart/liver ratios for the complexes described above. As can be seen from the data, the technetium-99m nitride heterocomplexes according to the present invention are markedly accumulated in heart and adrenal glands and their clearance from lungs and liver is rapid, so that high heart/lung and heart/liver ratios are attained. Thus, the technetium-99m nitride heterocomplexes according to the present invention have been proved to be useful for radiodiagnostic imaging of heart and adrenal glands.

The technetium-99m nitride heterocomplex according to the present invention can be formulated into a radiopharmaceutical for diagnostic imaging by its aseptic mixing with pharmaceutically acceptable additives, for example, stabilizers such as ascorbic acid and p-aminobenzoic acid; pH adjusters such as sodium carbonate buffer and sodium phosphate buffer; solubilizers such as α, β, γ-cyclodextrins, meglumine; and excipients such as D-mannitol. In addition, the radiopharmaceutical for diagnostic imaging of the present invention can be provided in the form of a kit for preparation at the time of use which is obtained by combining the technetium-99m nitride heterocomplex with the above additives.

The radiopharmaceutical for diagnostic imaging of the present invention can be administered by a conventional parenteral means such as intravenous administration, and the dosage thereof is determined depending on a radioactivity level at which imaging is considered possible, in view of the age and body weight of a patient, the condition of a disease to be cured, a radioactive imaging apparatus to be used, etc. When a radiopharmaceutical for diagnostic imaging obtained by using a substance labeled with technetium-99m is administered to a human being, the dosage thereof is 37 MBq to 1,850 MBq, preferably 185 MBq to 740 MBq, in terms of the radioactivity of technetium-99m. The radio-pharmaceutical for diagnostic imaging of the present invention had no acute toxicity so long as it was used in the dosage described above.

The technetium-99m nitride heterocomplex according to the present invention can easily be obtained by using a kit comprising components necessary for forming said complex. For example, there are prepared a vial 1 containing a nitrogen donor, a reducing agent, a stabilizer and a pH adjuster, and a vial 2 containing two different ligands, i.e., a bisphosphinoamine compound PNP and a bidentate ligand XY, and a solvent for PNP. Then, Na[$^{99m}$TcO$_4$] eluted from a $^{99}$Mo—$^{99m}$Tc generator is placed in the vial 1. On the other hand, physiological saline is placed in the vial 2 to dissolve the contents sufficiently, and a definite amount of the resulting solution is placed in the vial 1, followed by heating at about 100° C., whereby the technetium-99m nitride heterocomplex can be obtained.

The nitride nitrogen donor is a component necessary for forming technetium-99m nitride, and dithiocarbazic acid, dithiocarbazic acid derivatives, hydrazine, hydrazine derivatives, hydrazide derivatives, etc. are used as the nitrogen donor. As the reducing agent, stannous chloride, sodium hydrogensulfite and sodium borohydride, tertiary phosphines and tris-(m-sulfonatophenyl)phosphine etc. are used. As the stabilizer, ethylenediaminetetraacetic acid (EDTA) is preferable. As the pH adjuster, sodium phosphate buffer and sodium carbonate buffer are suitably used. Although depending on the ligand PNP, as a solubilizer for the ligand PNP and a surfactant to prevent attachment of the lipophilic Te-99m-nitride heterocomplex to the rubber and syringe walls, γ-cyclodextrin is suitably used.

Although the contents of each vial may be supplied in the form of a solution, their freeze-drying facilitates their storage and use.

The present invention is illustrated below in further detail with examples, but the present invention is not limited to the examples. Reagents, analytical methods and the like used in common in the following examples are described below together with their abbreviations.

(1) Bisphosphinoamine compound (PNP):
  PNP3; bis(dimethoxypropylphosphinoethyl)methoxyethyl-amine ($R^1$=a methoxypropyl group and $R^2$=a methoxyethyl group in the formula (1))
  PNP5; bis(dimethoxypropylphosphinoethyl)ethoxyethyl-amine ($R^1$=a methoxypropyl group and $R^2$=an ethoxyethyl group in the formula (1))
  PNP6; bis(diethoxypropylphosphinoethyl)-ethoxyethoxy-lamine ($R^1$=an ethoxypropyl group and $R^2$=an ethoxyethyl group in the formula (1))

(2) Physiologically active bidentate ligands (XY):
  DTC; N-methyl-S-methyl dithiocarbazate
  DMDC; N-dimethyl dithiocarbamate
  DEDC; N-diethyl dithiocarbamate
  DPDC; N-dipropyl dithiocarbamate
  NOME; N-methoxy-N-methyl dithiocarbamate
  NOET; N-ethoxy-N-ethyl dithiocarbamate
  PROME; N-methoxypropyl-N-ethyl dithiocarbamate
  ISOET; N-ethoxyethyl-N-isopropyl dithiocarbamate
  BOET; N-ethoxyethyl-N-ethyl dithiocarbamate
  POET; N-methoxyethyl-N-ethyl dithiocarbamate
  DPODC; N-dimethoxyethyl dithiocarbamate
  DBODC; N-diethoxyethyl dithiocarbamate (3) Reagents used for synthesizing complexes:
  SDH; succinic acid dihydrazide
  EDTA; ethylenediaminetetraacetic acid (4) Technetium-99m nitride heterocomplex:
  Abbreviated as $[^{99m}Tc(N) (PNP3) (XY)]^+$, $[^{99m}Tc(N) (PNP5) (XY)]^+$, $[^{99m}Tc(N) (PNP6) (XY)]^+$ or $^{99m}Tc(N)$ heterocomplex.

(5) Chromatographic analyses
  $^{99m}Tc(N)$ heterocomplexes subjected to experiments were analyzed by thin layer chromatography (TLC) and high performance liquid chromatography (HPLC). Conditions of each chromatography are as follows:

TLC:
  Cyclone Instrument (mfd. by Packard) equipped with a phosphor imaging screen for measuring apparatus and $SiO_2$-C18 stationary phase plates was used.

HPLC:
  Beckman System Gold apparatus (mfd. by Beckman) equipped with a Solvent Module 126, a scanning detector Module 166, a radioisotope detector Module 170, a reversed-phase C18 precolumn (Ultrasphere Beckman, 4.6×45 mm), a reversed-phase C18 column (Ultrasphere Beckman, 4.6×250 mm), and a 100-µL sample loop was used.

(6) Purification of complexes
  The $^{99m}Tc(N)$ heterocomplexes were purified as follows in order to remove the influences of impurities, before being used in analysis and biological evaluation.
  A cation exchange resin Sep-Pak cartridge (mfd. by Waters Millipore) was activated with 10.0 mL of deionized water. Then, a solution containing each $^{99m}Tc(N)$ heterocomplex was diluted with 8 mL of deionized water and passed through the cartridge. Onto the cartridge, 50 to 90% of the initial radioactivity was retained. After washing the cartridge with water and ethanol, the $^{99m}Tc(N)$ heterocomplex was recovered by passing ethanol/water (90/10) containing n-Bu$_4$NBr (0.1 M).

EXAMPLE 1

Synthesis of $^{99m}Tc(N)$ Heterocomplexes $^{99m}Tc(N)$ heterocomplexes were synthesized by the following three methods. The $^{99m}Tc(N)$ heterocomplexes could be similarly obtained by any of the methods and all of them had a radiochemical purity of 90 to 98% as determined by TLC.

Method 1:
  0.250 mL of Na[$^{99m}TcO_4$] (50.0 MBq to 3.0 GBq) eluted from a $^{99}Mo$—$^{99m}Tc$ generator was placed in a vial containing 5 mg of SDH, 5 mg of EDTA, $SnCl_2$ (suspended in 0.1 mL of physiological saline) and 1 mL of ethanol. After the vial was kept at room temperature for 30 min. a solution of 1 mg of PNP3, PNP5 or PNP6 in 0.250 mL of ethanol was added thereto and the vial was heated at 100° C. for 15 minutes. A solution of 1.0 mg of each predetermined bidentate ligand in 0.1 mL of physiological saline was added thereto and then the vial was heated at 100° C. for 15 minutes. Thus, monocationic $^{99m}Tc(N)$ heterocomplexes were obtained. The radiochemical purity of these complexes was 94 to 98% as determined by TLC.

Method 2:
  0.250 mL of Na[$^{99m}TcO_4$] (50.0 MBq to 3.0 GBq) eluted from a $^{99}Mo$—$^{99m}Tc$ generator was placed in a vial containing 5 mg of SDH, 5 mg of EDTA, $SnCl_2$ (suspended in 0.1 mL of physiological saline) and 1 mL of ethanol.
  After the vial was kept at room temperature for 30 minutes, a solution of 1.0 mg of each predetermined bidentate ligand in 0.1 mL of physiological saline was added thereto and then the vial was allowed to stand for 30 minutes. A solution of 1 mg of PNP3, PNP5 or PNP6 in 0.250 mL of ethanol was added to the vial, and the vial was heated at 100° C. for 15 minutes. Thus, monocationic $^{99m}Tc(N)$ heterocomplexes were obtained. The radiochemical purity of these complexes was 93 to 98% as determined by TLC.

Method 3:
  0.250 mL of Na[$^{99m}TcO_4$] (50.0 MBq to 3.0 GBq) eluted from a $^{99}Mo$—$^{99m}Tc$ generator was placed in a vial containing 5 mg of SDH, 5 mg of EDTA, $SnCl_2$ (suspended in 0.1 mL of physiological saline) and 1 mL of ethanol. After the vial was kept at room temperature for 30 minutes, a solution of 1.0 mg of each predetermined bidentate ligand in 0.1 mL of physiological saline and a solution of 1 mg of PNP3, PNP5 or PNP6 in 0.250 mL of ethanol was added thereto, followed by heating at 100° C. for 15 minutes. Thus, monocationic $^{99m}Tc(N)$ heterocomplexes were obtained. The radiochemical purity of these complexes was 90 to 95% as determined by TLC.

$^{99m}Tc(N)$ heterocomplexes were synthesized by the above method 1 by using PNP3, PNP5 or PNP6 as a bisphosphinoamine compound and DTC, DMDC, DEDC, DPDC, NOME, NOET, PROME, ISOET, BOET, POET, DPODC or DBODC bidentate ligand, and were used in the following examples.

EXAMPLE 2

Measurement of Log k' (Partition Ratio)

For the various $^{99m}Tc(N)$ heterocomplexes synthesized using PNP3 as a bisphosphinoamine compound in Example 1, Log k' values were determined at various compositions of a mobile phase for HPLC. As the mobile phase, mixtures of methanol and phosphate buffer (0.02M, pH=7.4) were used at a flow rate of 1.0 mL/min. For each sample, the retention time was measured at a minimum of three different methanol concentrations in the mobile phase. The Log k' values at 0% organic solvent (Log k'$_0$) were extrapolated from the linear part of the curve Log k'=a+bC, where C is the methanol concentration, and Log k' is Log (tR-to)/to wherein tR is HPLC retension time (min). The column void time (t$_o$) was regarded as being equal to the elution time of pertechnetic acid.

For the $^{99m}$Tc(N) heterocomplex of DTC, partition coefficient Log P was determined. The HPLC conditions were as follows; A: CH$_3$COONH$_4$ (0.01 M, pH=5) 10%, B: CH$_3$CN (THF 0.1%) 90%, C18, 0.5 mL/min. The measurement results are shown in Table 1.

EXAMPLE 3

Experiment for Confirming the Stability of the $^{99m}$Tc(N Heterocomplexes

The stability of the $^{99m}$Tc(N) heterocomplexes obtained using PNP3 as a bisphosphinoamine compound in Example 1 was confirmed by ligand exchange reaction with cysteine or glutathione.

250.0 μL of phosphate buffer solution (0.20 M, pH=7.4), 100 μL of water and 100 μL of each of the $^{99m}$Tc(N) heterocomplexes purified were mixed with 50 μL of each of cysteine solutions having different concentrations of 10 mM and 1.0 mM, and the resulting mixture was placed in a polypropylene test tube and incubated in a thermostat at 37° C. A blank solution was obtained by mixing an equal volume of water without addition of cysteine. Aliquots of the resulting solutions were withdrawn at 15 min, 30 min, 60 min and 2 hours after the start of the incubation, and analyzed by TLC. The same experiment as above was carried out except for using glutathione in place of cysteine. All the $^{99m}$Tc(N) heterocomplex samples were found stable against transchelation by cystein or glutathione. The experimental results are shown in Table 1.

TABLE 1

Log P or Log k' and stability of $^{99m}$Tc (N) heterocomplex

| No. of run | $^{99m}$Tc complex | Retention time (min) | Log P or Log k' | Stability |
|---|---|---|---|---|
| 1 | [$^{99m}$Tc (N) (PNP3) (DTC)$^+$] | 8.8 | 0.6 | Stable |
| 2 | [$^{99m}$Tc (N) (PNP3) (DMDC)$^+$] | 10.1 | 2.83 | Stable |
| 3 | [$^{99m}$Tc (N) (PNP3) (DEDC)$^+$] | 14.2 | 2.91 | Stable |
| 4 | [$^{99m}$Tc (N) (PNP3) (DPDC)$^+$] | 22.8 | 3.51 | Stable |
| 5 | [$^{99m}$Tc (N) (PNP3) (NOME)$^+$] | 10.3 | 2.84 | Stable |
| 6 | [$^{99m}$Tc (N) (PNP3) (NOET)$^+$] | 15.8 | 2.79 | Stable |
| 7 | [$^{99m}$Tc (N) (PNP3) (PROME)$^+$] | 14.0 | 3.28 | Stable |
| 8 | [$^{99m}$Tc (N) (PNP3) (BOET)$^+$] | 17.4 | 3.24 | Stable |
| 9 | [$^{99m}$Tc (N) (PNP3) (POET)$^+$] | 13.6 | 2.88 | Stable |
| 10 | [$^{99m}$Tc (N) (PNP3) (DPODC)$^+$] | 13.1 | 3.18 | Stable |
| 11 | [$^{99m}$Tc (N) (PNP3) (DBODC)$^+$] | 21.3 | 3.82 | Stable |

Note 1)
run No. 1: HPLC conditions; mobile phase A: CH$_3$COONH$_4$ (0.01M, pH = 5) 10%, B: CH$_3$CN(THF 0.1%) 90%, C18, 0.5 mL/min
Log P (partition coefficient) is shown.
Note 2)
run Nos 2 to 11: HPLC conditions; mobiule phase A: phosphate buffer (0.02M, pH = 7.4) 25%, B: CH$_3$OH 75%, C18, 1.0 mL/min
Log k' (partition ratio) is shown.

EXAMPLE 4

Measurement of Log k' and Rf

Log k'o values, measured at various compositions of the mobile phase, were determind for the $^{99m}$Tc(N) heterocomplexes obtained using PNP5 or PNP6 as a bisphosphinoamine compound. The analysis of the relationship between Log k'o values and the mobile-phase composition yielded extrapolated Log k' values as a measure of the partitioning between the hydrophobic stationary phase and water. The Log k' values were extrapolated from the linear part of the curve.

TLC chromatography was carried out on silica-gel plates and using the mixture ethanol/chloroform/toluene/[NH$_4$] [CH$_3$COO] (0.5 M) (5:3:3:0.5) as mobile phase. Activity was revealed using a Cyclone® instruments (Packard) equipped with a phosphor imaging screen and an OptiQuant software package. HPLC analysis was performed on a Beckman System Gold instrument equipped with a Programmable Solvent Module 126, a scanning detector Module 166 and a radioisotope detector Module 170. A C18 reversed-phase precolumn (Ultrasphere Beckman, 4.6×45 mm), a C18 reversed-phase column (Ultrasphere Beckman, 4.6×250 mm) and a 100-μL loop were used. The mobile phase was methanol in various mixtures (% v/v) with a phosphate buffer (pH=7.4, 0.02M) at a flow rate of 1.0 mL min$^{-1}$. Before injection, all solutions were purified using a C$_M$ Sep-Pak cartridge. The elution time (to) of a non-retained component was regarded as being equal to the elution time of sodium pertechnetate (2.77 min) The log k' values at 0% organic solvent (Log k'o) were extrapolated from the linear part of the curve Log k'=a+bC, where C is the methanol concentration and Log k'=Log (tR-to)/to(tR=HPLC retention time, min). Results for the $^{99m}$Tc(N) heterocomplexes are shown on Table 2.

TABLE 2

Log k' and Rf of $^{99m}$Tc (N) heterocomplex

| $^{99m}$Tc (N) heterocomplex | LOG k' | Rf |
|---|---|---|
| PNP5•DBODC | 3.69 | 0.65 |
| PNP5•NOME | 2.48 | 0.43 |
| PNP5•ISOET | — | 0.60 |
| PNP5•BOET | — | 0.54 |
| PNP6•DBODC | — | 0.80 |

EXAMPLE 5

Biodistribution of the $^{99m}$Tc(N) Heterocomiplexes

The biodistribution was measured by using female Sprague-Dawley rats (SD rats) weighing 200 g to 250 g. Each of the $^{99m}$Tc(N) heterocomplexes purified in the manner described above was diluted with phosphate buffer (0.1 M, pH=7.4) to obtain a final solution having an ethanol content of 10%. After the SD rats were anesthetized with an intramuscular injection of a mixture of ketamine (80 mg/kg) and xilazine (19 mg/kg), the jugular vein of each rat was surgically exposed and 100 μL (300 to 370 kBq) of the solution containing each $^{99m}$Tc(N) heterocomplexes prepared in the manner described above was injected in the jugular vein. The rats (n=3) were sacrificed by cervical dislocation at different times post injection. The blood was withdrawn from the heart through a syringe and counted. It was assumed that the whole blood content was 6.5% of the total body weight. The organs were excised from the rats, washed with physiological saline, weighed, and counted in a NaI well counter. Tables 3 to 18 show the results of the biodistribution measurement.

For comparison, Tables 19 and 20 show the results, obtained in the same manner as above, of measuring the biodistribution of ($^{99m}$Tc) (MIBI) and ($^{99m}$Tc) (Tf) which have been used as pharmaceuticals for diagnostic imaging for blood flow in myocardium.

Tables 21 to 23 show data showing the variations with time of heart accumulation, heart/lung ratios and heart/liver ratios for the $^{99m}$Tc(N) heterocomplexes of the present invention.

As can be seen from the data, the technetium-99m nitride heterocomplexes according to the present invention are markedly accumulated in heart and adrenal glands and their clearance from lungs and liver are rapid, so that high heart/lung and heart/liver ratios are attained. Thus, the technetium-99m nitride heterocomplexes according to the present invention have been proved to be useful for radiodiagnostic imaging of heart and adrenal glands.

TABLE 3

Biodistribution in rats of [$^{99m}$Tc(N) (PNP3) (DTC)]$^+$ (% ID/g)

| Organ | 0 min | 2 min | 10 min | 20 min | 30 min | 60 min | 120 min |
|---|---|---|---|---|---|---|---|
| Blood | 0.68 ± 0.20 | 0.26 ± 0.10 | 0.16 ± 0.00 | 0.04 ± 0.00 | 0.03 ± 0.00 | 0.02 ± 0.01 | 0.01 ± 0.00 |
| Submaxillary glands | 1.28 ± 0.42 | 1.48 ± 0.08 | 1.44 ± 0.07 | 1.36 ± 0.12 | 0.94 ± 0.22 | 1.29 ± 0.01 | 1.12 ± 0.12 |
| Brain | 0.11 ± 0.02 | 0.017 ± 0.004 | 0.010 ± 0.001 | 0.009 ± 0.001 | 0.007 ± 0.000 | 0.007 ± 0.002 | 0.005 ± 0.001 |
| Heart | 1.87 ± 0.02 | 2.17 ± 0.02 | 2.58 ± 0.09 | 2.02 ± 0.10 | 1.67 ± 0.05 | 2.20 ± 0.10 | 2.23 ± 0.19 |
| Lungs | 1.27 ± 0.20 | 0.73 ± 0.10 | 0.62 ± 0.05 | 0.48 ± 0.07 | 0.38 ± 0.00 | 0.18 ± 0.04 | 0.27 ± 0.00 |
| Liver | 2.26 ± 0.36 | 3.46 ± 0.16 | 2.23 ± 0.50 | 0.77 ± 0.22 | 0.60 ± 0.10 | 0.23 ± 0.03 | 0.24 ± 0.04 |
| Spleen | 0.93 ± 0.20 | 0.68 ± 0.05 | 0.55 ± 0.03 | 0.39 ± 0.06 | 0.28 ± 0.01 | 0.24 ± 0.04 | 0.16 ± 0.03 |
| Adrenal Glands | 1.71 ± 0.64 | 1.52 ± 0.11 | 1.08 ± 0.07 | 1.29 ± 0.13 | 0.76 ± 0.16 | 0.94 ± 0.08 | 0.39 ± 0.02 |
| Kidneys | 9.39 ± 1.29 | 8.57 ± 0.89 | 6.51 ± 1.08 | 4.44 ± 0.69 | 3.64 ± 0.04 | 3.30 ± 0.06 | 3.03 ± 0.32 |
| Intestine | 2.99 ± 0.36 | 4.45 ± 0.90 | 15.34 ± 0.89 | 12.25 ± 0.82 | 10.43 ± 0.23 | 9.94 ± 0.29 | 3.04 ± 0.48 |
| Muscle | 0.16 ± 0.02 | 0.21 ± 0.00 | 0.18 ± 0.01 | 0.12 ± 0.03 | 0.18 ± 0.04 | 0.17 ± 0.01 | 0.13 ± 0.01 |

TABLE 4

Biodistribution in rats of [$^{99m}$Tc(N) (PNP3) (DEDC)]$^+$ (% ID/g)

| Organ | 0 min | 2 min | 10 min | 20 min | 30 min | 60 min | 120 min |
|---|---|---|---|---|---|---|---|
| Blood | 0.42 ± 0.03 | 0.19 ± 0.01 | 0.06 ± 0.01 | 0.05 ± 0.01 | 0.02 ± 0.00 | 0.015 ± 0.001 | 0.010 ± 0.000 |
| Submaxillary glands | 1.26 ± 0.32 | 1.24 ± 0.18 | 1.16 ± 0.13 | 1.05 ± 0.13 | 0.99 ± 0.08 | 1.13 ± 0.12 | 1.66 ± 0.09 |
| Brain | 0.11 ± 0.03 | 0.02 ± 0.00 | 0.02 ± 0.00 | 0.010 ± 0.000 | 0.012 ± 0.005 | 0.012 ± 0.002 | 0.005 ± 0.001 |
| Heart | 2.74 ± 0.10 | 2.55 ± 0.02 | 2.84 ± 0.00 | 2.90 ± 0.09 | 2.26 ± 0.20 | 2.50 ± 0.04 | 2.85 ± 0.04 |
| Lungs | 1.69 ± 0.34 | 0.85 ± 0.05 | 0.92 ± 0.10 | 0.94 ± 0.01 | 0.59 ± 0.08 | 0.52 ± 0.03 | 0.51 ± 0.02 |
| Liver | 1.78 ± 0.23 | 3.69 ± 0.80 | 1.64 ± 0.19 | 0.93 ± 0.05 | 0.34 ± 0.05 | 0.19 ± 0.01 | 0.14 ± 0.02 |
| Spleen | 2.26 ± 0.24 | 0.88 ± 0.10 | 0.19 ± 0.02 | 0.96 ± 0.02 | 0.64 ± 0.04 | 0.52 ± 0.09 | 0.36 ± 0.06 |
| Adrenal Glands | 3.29 ± 0.62 | 2.54 ± 0.12 | 1.86 ± 0.02 | 3.34 ± 0.48 | 1.79 ± 0.32 | 2.16 ± 0.62 | 3.46 ± 0.43 |
| Kidneys | 10.15 ± 0.66 | 11.21 ± 1.12 | 7.59 ± 1.30 | 7.00 ± 0.40 | 4.64 ± 0.36 | 4.28 ± 0.15 | 4.28 ± 0.06 |
| Intestine | 4.48 ± 1.44 | 4.25 ± 0.60 | 13.65 ± 2.55 | 13.34 ± 3.81 | 7.87 ± 3.81 | 6.26 ± 1.86 | 6.95 ± 3.71 |
| Muscle | 0.015 ± 0.04 | 0.16 ± 0.02 | 0.12 ± 0.03 | 0.13 ± 0.02 | 0.16 ± 0.04 | 0.18 ± 0.02 | 0.17 ± 0.02 |

TABLE 5

Biodistribution in rats of [$^{99m}$Tc(N) (PNP3) (NOET)]$^+$ (% ID/g)

| Organ | 0 min | 2 min | 10 min | 20 min | 30 min | 60 min | 120 min |
|---|---|---|---|---|---|---|---|
| Blood | 0.26 ± 0.01 | 0.15 ± 0.02 | 0.05 ± 0.02 | 0.02 ± 0.00 | 0.03 ± 0.01 | 0.01 ± 0.00 | 0.01 ± 0.00 |
| Submaxillary glands | 2.13 ± 0.16 | 1.10 ± 0.14 | 1.11 ± 0.16 | 1.34 ± 0.14 | 1.06 ± 0.21 | 1.39 ± 0.21 | 1.66 ± 0.35 |
| Brain | 0.10 ± 0.01 | 0.02 ± 0.01 | 0.02 ± 0.01 | 0.01 ± 0.00 | 0.01 ± 0.00 | 0.01 ± 0.00 | 0.01 ± 0.00 |
| Heart | 2.93 ± 0.02 | 2.87 ± 0.14 | 2.86 ± 0.40 | 3.11 ± 0.77 | 2.97 ± 0.43 | 2.42 ± 0.19 | 2.78 ± 0.21 |
| Lungs | 1.29 ± 0.20 | 0.82 ± 0.09 | 0.63 ± 0.02 | 0.57 ± 0.17 | 0.60 ± 0.03 | 0.38 ± 0.09 | 0.34 ± 0.06 |
| Liver | 1.56 ± 0.12 | 2.65 ± 0.17 | 1.36 ± 0.39 | 0.68 ± 0.23 | 0.54 ± 0.08 | 0.18 ± 0.12 | 0.09 ± 0.02 |
| Spleen | 1.76 ± 0.36 | 1.44 ± 0.12 | 1.20 ± 0.21 | 0.72 ± 0.12 | 1.02 ± 0.31 | 0.40 ± 0.02 | 0.41 ± 0.06 |
| Adrenal Glands | 2.25 ± 0.42 | 2.08 ± 0.58 | 2.07 ± 0.60 | 1.75 ± 0.32 | 1.87 ± 0.38 | 1.55 ± 0.12 | 1.82 ± 0.70 |
| Kidneys | 10.0 ± 0.40 | 10.6 ± 1.08 | 6.11 ± 1.08 | 4.88 ± 1.02 | 5.54 ± 0.63 | 3.28 ± 0.47 | 3.77 ± 0.49 |
| Intestine | 3.92 ± 0.94 | 6.84 ± 0.70 | 7.15 ± 1.46 | 8.78 ± 3.90 | 11.03 ± 3.80 | 5.53 ± 2.84 | 5.22 ± 3.07 |
| Muscle | 0.20 ± 0.01 | 0.17 ± 0.03 | 0.11 ± 0.04 | 0.17 ± 0.04 | 0.12 ± 0.01 | 0.15 ± 0.04 | 0.16 ± 0.02 |

TABLE 6

Biodistribution in rats of [$^{99m}$Tc(N) (PNP3) (DMDC)]$^+$ (% ID/g)

| Organ | 0 min | 2 min | 10 min | 20 min | 30 min | 60 min | 120 min |
|---|---|---|---|---|---|---|---|
| Blood | 0.73 ± 0.24 | 0.21 ± 0.04 | 0.05 ± 0.01 | 0.04 ± 0.01 | 0.03 ± 0.01 | 0.02 ± 0.00 | 0.01 ± 0.00 |
| Submaxillary glands | 1.19 ± 0.38 | 1.50 ± 0.15 | 1.44 ± 0.12 | 1.73 ± 0.24 | 1.31 ± 0.14 | 1.50 ± 0.22 | 1.51 ± 0.10 |
| Brain | 0.16 ± 0.02 | 0.02 ± 0.01 | 0.02 ± 0.00 | 0.01 ± 0.00 | 0.01 ± 0.00 | 0.00 ± 0.00 | 0.00 ± 0.00 |
| Heart | 2.55 ± 0.26 | 2.41 ± 0.14 | 2.45 ± 0.23 | 2.39 ± 0.22 | 2.17 ± 0.07 | 2.55 ± 0.18 | 2.33 ± 0.26 |
| Lungs | 1.17 ± 0.13 | 0.86 ± 0.11 | 0.54 ± 0.08 | 0.38 ± 0.03 | 0.33 ± 0.01 | 0.23 ± 0.01 | 0.18 ± 0.02 |
| Liver | 2.59 ± 0.96 | 3.48 ± 0.72 | 1.08 ± 0.24 | 0.71 ± 0.23 | 0.65 ± 0.49 | 0.18 ± 0.03 | 0.09 ± 0.01 |

TABLE 6-continued

Biodistribution in rats of [$^{99m}$Tc(N) (PNP3) (DMDC)]$^+$ (% ID/g)

| Organ | 0 min | 2 min | 10 min | 20 min | 30 min | 60 min | 120 min |
|---|---|---|---|---|---|---|---|
| Spleen | 1.37 ± 0.29 | 0.66 ± 0.16 | 0.38 ± 0.05 | 0.26 ± 0.01 | 0.21 ± 0.02 | 0.13 ± 0.02 | 0.07 ± 0.02 |
| Adrenal Glands | 1.21 ± 0.25 | 1.14 ± 0.14 | 1.51 ± 0.29 | 1.00 ± 0.20 | 1.04 ± 0.25 | 1.09 ± 0.28 | 1.04 ± 0.03 |
| Kidneys | 7.86 ± 1.48 | 9.71 ± 1.29 | 4.84 ± 1.19 | 3.85 ± 0.45 | 3.62 ± 0.73 | 2.96 ± 0.37 | 2.36 ± 0.89 |
| Intestine | 4.44 ± 0.57 | 3.71 ± 1.31 | 13.54 ± 3.02 | 12.96 ± 1.59 | 11.87 ± 3.34 | 8.22 ± 5.24 | 3.05 ± 0.99 |
| Muscle | 0.27 ± 0.11 | 0.20 ± 0.02 | 0.35 ± 0.19 | 0.27 ± 0.07 | 0.26 ± 0.06 | 0.28 ± 0.04 | 0.31 ± 0.05 |

TABLE 7

Biodistribution in rats of [$^{99m}$Tc(N) (PNP3) (NOME)]$^+$ (% ID/g)

| Organ | 0 min | 2 min | 10 min | 20 min | 30 min | 60 min | 120 min |
|---|---|---|---|---|---|---|---|
| Blood | 0.64 ± 0.15 | 0.14 ± 0.01 | 0.04 ± 0.00 | 0.03 ± 0.00 | 0.03 ± 0.00 | 0.01 ± 0.00 | 0.01 ± 0.00 |
| Submaxillary glands | 0.76 ± 0.01 | 0.76 ± 0.13 | 0.88 ± 0.15 | 1.00 ± 0.09 | 0.84 ± 0.04 | 0.80 ± 0.11 | 0.74 ± 0.14 |
| Brain | 0.16 ± 0.05 | 0.02 ± 0.00 | 0.01 ± 0.00 | 0.00 ± 0.00 | 0.00 ± 0.00 | 0.00 ± 0.00 | 0.00 ± 0.00 |
| Heart | 1.23 ± 0.09 | 1.16 ± 0.06 | 1.13 ± 0.07 | 1.15 ± 0.08 | 1.33 ± 0.10 | 1.31 ± 0.05 | 1.16 ± 0.04 |
| Lungs | 0.66 ± 0.03 | 0.36 ± 0.03 | 0.30 ± 0.02 | 0.26 ± 0.01 | 0.28 ± 0.01 | 0.21 ± 0.03 | 0.16 ± 0.02 |
| Liver | 1.24 ± 0.04 | 1.75 ± 0.16 | 0.76 ± 0.10 | 0.54 ± 0.03 | 0.30 ± 0.02 | 0.12 ± 0.02 | 0.07 ± 0.01 |
| Spleen | 0.60 ± 0.02 | 0.31 ± 0.02 | 0.24 ± 0.01 | 0.17 ± 0.00 | 0.20 ± 0.01 | 0.14 ± 0.02 | 0.08 ± 0.02 |
| Adrenal Glands | 0.61 ± 0.02 | 0.57 ± 0.16 | 0.55 ± 0.03 | 0.64 ± 0.08 | 0.54 ± 0.11 | 0.66 ± 0.23 | 0.66 ± 0.06 |
| Kidneys | 0.258 ± 0.15 | 4.60 ± 0.34 | 2.26 ± 0.35 | 1.94 ± 0.35 | 2.23 ± 0.06 | 1.93 ± 0.27 | 1.66 ± 0.23 |
| Intestine | 1.10 ± 0.09 | 2.52 ± 0.44 | 5.92 ± 2.66 | 8.43 ± 0.67 | 6.52 ± 1.16 | 4.53 ± 1.21 | 3.86 ± 1.72 |
| Muscle | 0.11 ± 0.08 | 0.11 ± 0.00 | 0.16 ± 0.03 | 0.15 ± 0.01 | 0.14 ± 0.01 | 0.11 ± 0.01 | 0.12 ± 0.01 |

TABLE 8

Biodistribution in rats of [$^{99m}$Tc(N) (PNP3) (DPDC)]$^+$ (% ID/g)

| Organ | 0 min | 2 min | 10 min | 20 min | 30 min | 60 min | 120 min |
|---|---|---|---|---|---|---|---|
| Blood | 0.74 ± 0.08 | 0.11 ± 0.03 | 0.03 ± 0.01 | 0.02 ± 0.01 | 0.02 ± 0.00 | 0.02 ± 0.00 | 0.01 ± 0.00 |
| Submaxillary glands | 0.88 ± 0.20 | 0.70 ± 0.01 | 0.86 ± 0.14 | 0.93 ± 0.16 | 0.77 ± 0.06 | 0.72 ± 0.04 | 0.86 ± 0.18 |
| Brain | 0.08 ± 0.01 | 0.02 ± 0.01 | 0.02 ± 0.01 | 0.01 ± 0.00 | 0.01 ± 0.00 | 0.01 ± 0.00 | 0.00 ± 0.00 |
| Heart | 2.50 ± 0.23 | 2.09 ± 0.18 | 1.92 ± 0.28 | 1.76 ± 0.07 | 1.50 ± 0.06 | 1.74 ± 0.17 | 1.66 ± 0.16 |
| Lungs | 0.83 ± 0.10 | 0.64 ± 0.11 | 0.44 ± 0.05 | 0.42 ± 0.05 | 0.28 ± 0.02 | 0.34 ± 0.02 | 0.24 ± 0.05 |
| Liver | 0.57 ± 0.10 | 1.70 ± 0.51 | 1.13 ± 0.28 | 0.72 ± 0.14 | 0.43 ± 0.03 | 0.17 ± 0.05 | 0.07 ± 0.01 |
| Spleen | 0.97 ± 0.23 | 1.36 ± 0.20 | 1.27 ± 0.18 | 1.20 ± 0.16 | 0.78 ± 0.12 | 0.76 ± 0.18 | 0.56 ± 0.02 |
| Adrenal Glands | 2.94 ± 0.88 | 1.97 ± 0.02 | 2.26 ± 0.41 | 2.38 ± 0.26 | 2.15 ± 0.41 | 2.21 ± 0.56 | 2.57 ± 0.71 |
| Kidneys | 5.78 ± 1.97 | 6.19 ± 2.31 | 5.22 ± 2.39 | 5.62 ± 0.75 | 5.02 ± 1.34 | 3.93 ± 1.18 | 3.75 ± 0.24 |
| Intestine | 1.90 ± 0.48 | 2.68 ± 0.77 | 4.37 ± 2.13 | 5.06 ± 0.94 | 4.79 ± 2.32 | 7.68 ± 3.34 | 2.34 ± 1.44 |
| Muscle | 0.15 ± 0.05 | 0.11 ± 0.06 | 0.11 ± 0.03 | 0.11 ± 0.03 | 0.10 ± 0.02 | 0.10 ± 0.02 | 0.08 ± 0.02 |

TABLE 9

Biodistribution in rats of [$^{99m}$Tc(N) (PNP3) (DPODC)]$^+$ (% ID/g)

| Organ | 0 min | 2 min | 10 min | 20 min | 30 min | 60 min | 120 min |
|---|---|---|---|---|---|---|---|
| Blood | 1.36 ± 0.02 | 0.30 ± 0.09 | 0.21 ± 0.00 | 0.08 ± 0.02 | 0.04 ± 0.00 | 0.02 ± 0.01 | 0.01 ± 0.00 |
| Submaxillary glands | 2.27 ± 0.20 | 1.22 ± 0.11 | 1.70 ± 0.60 | 1.38 ± 0.07 | 1.53 ± 0.17 | 1.33 ± 0.46 | 1.36 ± 0.14 |
| Brain | 0.20 ± 0.02 | 0.02 ± 0.00 | 0.01 ± 0.00 | 0.01 ± 0.00 | 0.01 ± 0.00 | 0.01 ± 0.00 | 0.01 ± 0.00 |
| Heart | 3.08 ± 0.31 | 2.06 ± 0.13 | 2.37 ± 0.33 | 2.49 ± 0.31 | 2.57 ± 0.06 | 2.26 ± 0.60 | 2.45 ± 0.41 |
| Lungs | 1.45 ± 0.04 | 0.65 ± 0.06 | 0.67 ± 0.23 | 0.43 ± 0.05 | 0.41 ± 0.04 | 0.27 ± 0.09 | 0.20 ± 0.04 |
| Liver | 3.48 ± 0.24 | 3.71 ± 0.36 | 3.49 ± 0.09 | 1.86 ± 0.47 | 1.30 ± 0.71 | 0.42 ± 0.23 | 0.16 ± 0.04 |
| Spleen | 1.23 ± 0.01 | 0.51 ± 0.04 | 0.57 ± 0.22 | 0.38 ± 0.04 | 0.37 ± 0.00 | 0.18 ± 0.10 | 0.14 ± 0.03 |
| Adrenal Glands | 1.65 ± 0.22 | 0.98 ± 0.12 | 1.49 ± 0.82 | 1.46 ± 0.15 | 1.31 ± 0.19 | 1.17 ± 0.17 | 1.14 ± 0.15 |
| Kidneys | 6.36 ± 0.13 | 8.21 ± 0.62 | 6.82 ± 3.62 | 5.63 ± 2.05 | 4.88 ± 0.56 | 3.44 ± 0.76 | 3.43 ± 0.38 |
| Intestine | 3.25 ± 0.60 | 4.30 ± 1.74 | 4.36 ± 2.28 | 14.47 ± 4.75 | 11.78 ± 1.78 | 11.05 ± 5.05 | 16.10 ± 2.10 |
| Muscle | 0.27 ± 0.02 | 0.25 ± 0.04 | 0.29 ± 0.08 | 0.39 ± 0.12 | 0.32 ± 0.08 | 0.27 ± 0.04 | 0.36 ± 0.12 |

TABLE 10

Biodistribution in rats of [$^{99m}$Tc(N) (PNP3) (DBODC)]$^+$ (% ID/g)

| Organ | 0 min | 2 min | 10 min | 20 min | 30 min | 60 min | 120 min |
|---|---|---|---|---|---|---|---|
| Blood | 0.55 ± 0.32 | 0.11 ± 0.01 | 0.03 ± 0.00 | 0.02 ± 0.01 | 0.02 ± 0.00 | 0.01 ± 0.00 | 0.01 ± 0.00 |
| Submaxillary glands | 1.25 ± 0.47 | 1.27 ± 0.05 | 1.42 ± 0.24 | 1.32 ± 0.21 | 1.49 ± 0.22 | 1.29 ± 0.28 | 1.59 ± 0.19 |
| Brain | 0.23 ± 0.04 | 0.03 ± 0.00 | 0.02 ± 0.00 | 0.02 ± 0.01 | 0.02 ± 0.02 | 0.01 ± 0.00 | 0.01 ± 0.00 |
| Heart | 3.57 ± 0.14 | 3.42 ± 0.19 | 3.65 ± 0.56 | 3.32 ± 0.18 | 3.27 ± 0.36 | 3.27 ± 0.62 | 3.00 ± 0.42 |
| Lungs | 1.54 ± 0.03 | 1.01 ± 0.49 | 0.77 ± 0.10 | 0.84 ± 0.06 | 0.69 ± 0.12 | 0.34 ± 0.11 | 0.27 ± 0.05 |
| Liver | 1.46 ± 0.05 | 1.72 ± 0.26 | 1.43 ± 0.47 | 0.87 ± 0.52 | 0.42 ± 0.01 | 0.16 ± 0.05 | 0.12 ± 0.03 |
| Spleen | 1.84 ± 0.49 | 2.00 ± 0.07 | 1.28 ± 0.12 | 0.92 ± 0.10 | 0.95 ± 0.02 | 0.42 ± 0.11 | 0.21 ± 0.03 |
| Adrenal Glands | 2.68 ± 0.44 | 2.87 ± 1.00 | 2.30 ± 0.73 | 2.69 ± 0.37 | 2.94 ± 0.18 | 2.17 ± 0.35 | 2.53 ± 0.27 |
| Kidneys | 10.40 ± 2.16 | 11.57 ± 2.37 | 6.74 ± 0.63 | 6.12 ± 0.11 | 5.67 ± 0.39 | 4.24 ± 0.53 | 3.48 ± 0.61 |
| Intestine | 2.43 ± 0.49 | 7.42 ± 1.03 | 12.11 ± 2.92 | 13.03 ± 3.19 | 13.41 ± 4.62 | 4.39 ± 2.86 | 7.03 ± 2.61 |
| Muscle | 0.23 ± 0.04 | 0.23 ± 0.01 | 0.23 ± 0.07 | 0.13 ± 0.02 | 0.24 ± 0.08 | 0.17 ± 0.01 | 0.36 ± 0.15 |

TABLE 11

Biodistribution in rats of [$^{99m}$Tc(N) (PNP3) (BOET)]$^+$ (% ID/g)

| Organ | 0 min | 2 min | 10 min | 20 min | 30 min | 60 min | 120 min |
|---|---|---|---|---|---|---|---|
| Blood | 0.40 ± 0.15 | 0.16 ± 0.02 | 0.06 ± 0.02 | 0.03 ± 0.00 | 0.02 ± 0.01 | 0.02 ± 0.00 | 0.01 ± 0.00 |
| Submaxillary glands | 1.32 ± 0.45 | 1.26 ± 0.19 | 1.14 ± 0.14 | 1.08 ± 0.13 | 1.27 ± 0.35 | 1.34 ± 0.29 | 1.11 ± 0.18 |
| Brain | 0.21 ± 0.05 | 0.03 ± 0.00 | 0.02 ± 0.00 | 0.01 ± 0.00 | 0.01 ± 0.00 | 0.01 ± 0.00 | 0.00 ± 0.00 |
| Heart | 3.24 ± 0.78 | 3.14 ± 0.08 | 2.88 ± 0.33 | 3.09 ± 0.19 | 2.89 ± 0.18 | 2.84 ± 0.06 | 3.00 ± 0.24 |
| Lungs | 0.98 ± 0.27 | 0.98 ± 0.23 | 0.69 ± 0.11 | 0.61 ± 0.15 | 0.44 ± 0.06 | 0.40 ± 0.07 | 0.22 ± 0.05 |
| Liver | 1.87 ± 0.19 | 2.03 ± 0.24 | 1.22 ± 0.28 | 0.72 ± 0.14 | 0.45 ± 0.07 | 0.26 ± 0.03 | 0.12 ± 0.03 |
| Spleen | 2.14 ± 0.68 | 1.53 ± 0.17 | 1.14 ± 0.14 | 0.84 ± 0.06 | 0.62 ± 0.08 | 0.46 ± 0.07 | 0.40 ± 0.02 |
| Adrenal Glands | 2.59 ± 0.73 | 2.77 ± 0.49 | 2.56 ± 0.20 | 2.34 ± 0.81 | 2.35 ± 0.24 | 2.04 ± 0.35 | 2.42 ± 0.22 |
| Kidneys | 10.12 ± 1.80 | 12.13 ± 1.80 | 7.92 ± 1.01 | 5.22 ± 2.09 | 5.66 ± 0.46 | 3.66 ± 0.50 | 3.81 ± 0.10 |
| Intestine | 3.45 ± 0.46 | 4.68 ± 1.28 | 8.61 ± 2.43 | 12.25 ± 2.29 | 9.18 ± 6.12 | 8.78 ± 1.91 | 9.42 ± 0.81 |
| Muscle | 0.19 ± 0.04 | 0.20 ± 0.04 | 0.16 ± 0.07 | 0.15 ± 0.02 | 0.26 ± 0.04 | 0.21 ± 0.02 | 0.19 ± 0.05 |

TABLE 12

Biodistribution in rats of [$^{99m}$Tc(N) (PNP3) (POET)]$^+$ (% ID/g)

| Organ | 0 min | 2 min | 10 min | 20 min | 30 min | 60 min | 120 min |
|---|---|---|---|---|---|---|---|
| Blood | 0.40 ± 0.20 | 0.13 ± 0.02 | 0.04 ± 0.00 | 0.03 ± 0.00 | 0.03 ± 0.01 | 0.01 ± 0.00 | 0.01 ± 0.00 |
| Submaxillary glands | 1.01 ± 0.32 | 1.19 ± 0.03 | 1.30 ± 0.12 | 1.21 ± 0.13 | 1.28 ± 0.19 | 1.27 ± 0.07 | 1.19 ± 0.04 |
| Brain | 0.20 ± 0.07 | 0.02 ± 0.00 | 0.01 ± 0.00 | 0.02 ± 0.00 | 0.01 ± 0.00 | 0.01 ± 0.00 | 0.01 ± 0.00 |
| Heart | 2.21 ± 0.23 | 2.65 ± 0.26 | 2.49 ± 0.09 | 2.45 ± 0.24 | 2.31 ± 0.09 | 2.37 ± 0.18 | 2.41 ± 0.17 |
| Lungs | 0.85 ± 0.29 | 0.67 ± 0.08 | 0.55 ± 0.03 | 0.47 ± 0.06 | 0.42 ± 0.02 | 0.34 ± 0.06 | 0.22 ± 0.02 |
| Liver | 1.70 ± 0.29 | 2.39 ± 0.41 | 1.74 ± 0.22 | 0.86 ± 0.29 | 0.44 ± 0.09 | 0.18 ± 0.05 | 0.09 ± 0.02 |
| Spleen | 1.08 ± 0.36 | 0.96 ± 0.12 | 0.65 ± 0.05 | 0.53 ± 0.03 | 0.46 ± 0.07 | 0.30 ± 0.06 | 0.15 ± 0.01 |
| Adrenal Glands | 1.62 ± 0.52 | 1.79 ± 0.16 | 1.79 ± 0.39 | 1.79 ± 0.73 | 1.76 ± 0.23 | 1.99 ± 0.39 | 1.82 ± 0.25 |
| Kidneys | 7.36 ± 1.08 | 9.94 ± 1.22 | 5.40 ± 0.27 | 5.27 ± 0.85 | 4.29 ± 0.61 | 3.41 ± 0.71 | 2.45 ± 0.29 |
| Intestine | 2.57 ± 0.57 | 4.05 ± 0.70 | 5.11 ± 1.86 | 8.87 ± 3.00 | 13.51 ± 3.87 | 9.88 ± 1.81 | 7.02 ± 1.78 |
| Muscle | 0.19 ± 0.05 | 0.17 ± 0.02 | 0.16 ± 0.04 | 0.21 ± 0.11 | 0.19 ± 0.08 | 0.17 ± 0.03 | 0.26 ± 0.04 |

TABLE 13

Biodistribution in rats of [$^{99m}$Tc(N) (PNP3) (PROME)]$^+$ (% ID/g)

| Organ | 0 min | 2 min | 10 min | 20 min | 30 min | 60 min | 120 min |
|---|---|---|---|---|---|---|---|
| Blood | 0.59 ± 0.07 | 0.15 ± 0.02 | 0.07 ± 0.05 | 0.03 ± 0.00 | 0.04 ± 0.02 | 0.02 ± 0.00 | 0.02 ± 0.01 |
| Submaxillary glands | 1.70 ± 0.35 | 1.51 ± 0.03 | 1.44 ± 0.15 | 1.41 ± 0.11 | 1.46 ± 0.52 | 1.46 ± 0.22 | 1.59 ± 0.31 |
| Brain | 0.17 ± 0.06 | 0.02 ± 0.00 | 0.01 ± 0.00 | 0.01 ± 0.00 | 0.01 ± 0.00 | 0.00 ± 0.00 | 0.00 ± 0.00 |
| Heart | 2.62 ± 0.06 | 2.76 ± 0.47 | 2.33 ± 0.33 | 2.46 ± 0.15 | 2.62 ± 0.35 | 2.41 ± 0.32 | 2.71 ± 0.23 |
| Lungs | 1.09 ± 0.17 | 0.84 ± 0.08 | 0.56 ± 0.05 | 0.47 ± 0.02 | 0.31 ± 0.07 | 0.21 ± 0.05 | 0.18 ± 0.00 |
| Liver | 1.65 ± 0.11 | 2.04 ± 0.24 | 1.53 ± 0.54 | 0.68 ± 0.05 | 0.41 ± 0.14 | 0.12 ± 0.02 | 0.10 ± 0.01 |
| Spleen | 1.32 ± 0.07 | 0.99 ± 0.07 | 0.71 ± 0.04 | 0.51 ± 0.01 | 0.31 ± 0.06 | 0.15 ± 0.04 | 0.12 ± 0.01 |
| Adrenal Glands | 1.81 ± 0.06 | 2.72 ± 0.51 | 2.08 ± 0.49 | 2.03 ± 0.45 | 1.45 ± 0.06 | 1.88 ± 0.25 | 1.61 ± 0.28 |
| Kidneys | 7.99 ± 0.11 | 10.31 ± 1.05 | 6.01 ± 1.55 | 4.14 ± 0.06 | 3.10 ± 1.83 | 2.62 ± 0.50 | 2.71 ± 0.57 |
| Intestine | 2.84 ± 0.46 | 5.52 ± 1.16 | 8.15 ± 1.02 | 7.22 ± 0.56 | 10.76 ± 2.35 | 6.66 ± 1.16 | 7.85 ± 1.25 |
| Muscle | 0.17 ± 0.04 | 0.18 ± 0.00 | 0.19 ± 0.02 | 0.19 ± 0.04 | 0.23 ± 0.07 | 0.19 ± 0.05 | 0.18 ± 0.03 |

TABLE 14

Biodistribution in rats of the complex [$^{99m}$Tc(N) (PNP5) (DBODC)]$^+$ (% dose/g)

| Organ | 0 min | 2 min | 10 min | 20 min | 30 min | 60 min | 120 min. |
|---|---|---|---|---|---|---|---|
| Blood | 6.65 ± 0.50 | 0.11 ± 0.02 | 0.03 ± 0.01 | 0.02 ± 0.00 | 0.02 ± 0.00 | 0.01 ± 0.00 | 0.01 ± 0.00 |
| Submax. glands | 0.16 ± 0.02 | 1.77 ± 0.18 | 1.79 ± 0.23 | 1.57 ± 0.23 | 1.88 ± 0.50 | 1.84 ± 0.10 | 2.09 ± 0.14 |
| Brain | 0.45 ± 0.09 | 0.03 ± 0.00 | 0.01 ± 0.00 | 0.01 ± 0.01 | 0.01 ± 0.00 | 0.01 ± 0.00 | 0.00 ± 0.00 |
| Heart | 5.01 ± 0.16 | 3.94 ± 0.32 | 3.69 ± 0.29 | 3.63 ± 0.46 | 3.73 ± 0.48 | 3.76 ± 0.39 | 3.31 ± 0.06 |
| Lungs | 6.58 ± 1.09 | 0.99 ± 0.36 | 0.88 ± 0.03 | 0.57 ± 0.08 | 0.64 ± 0.13 | 0.46 ± 0.07 | 0.25 ± 0.01 |
| Liver | 0.82 ± 0.09 | 2.66 ± 0.88 | 1.61 ± 0.21 | 0.96 ± 0.09 | 0.72 ± 0.06 | 0.20 ± 0.05 | 0.10 ± 0.03 |
| Spleen | 1.75 ± 0.21 | 2.68 ± 0.45 | 1.79 ± 0.31 | 1.41 ± 0.12 | 0.92 ± 0.34 | 0.41 ± 0.30 | 0.21 ± 0.06 |
| Adrenal glands | 2.87 ± 0.37 | 3.95 ± 0.76 | 3.73 ± 1.03 | 3.00 ± 0.55 | 3.36 ± 0.05 | 4.17 ± 0.48 | 3.44 ± 0.88 |
| Kidneys | 3.71 ± 2.38 | 14.69 ± 2.30 | 9.16 ± 1.08 | 6.58 ± 0.80 | 6.70 ± 0.98 | 5.73 ± 0.55 | 3.48 ± 0.14 |
| Intestine | 1.71 ± 1.33 | 7.97 ± 0.94 | 9.04 ± 1.71 | 9.63 ± 1.60 | 6.70 ± 0.71 | 6.52 ± 7.65 | 6.57 ± 5.38 |
| Muscle | 0.09 ± 0.11 | 0.20 ± 0.04 | 0.21 ± 0.05 | 0.17 ± 0.02 | 0.19 ± 0.04 | 0.21 ± 0.03 | 0.23 ± 0.06 |

TABLE 15

Biodistribution in rats of the complex [$^{99m}$Tc(N) (PNP5) (NOME)]$^+$ (% dose/g)

| Organ | 0 min | 2 min | 10 min | 20 min | 30 min | 60 min | 120 min. |
|---|---|---|---|---|---|---|---|
| Blood | 2.18 ± 0.74 | 0.15 ± 0.01 | 0.07 ± 0.01 | 0.03 ± 0.00 | 0.03 ± 0.01 | 0.02 ± 0.00 | 0.01 ± 0.00 |
| Submax. glands | 1.41 ± 0.50 | 2.34 ± 0.09 | 2.16 ± 0.09 | 1.78 ± 0.18 | 1.99 ± 0.18 | 1.88 ± 0.47 | 1.95 ± 0.19 |
| Brain | 0.08 ± 0.02 | 0.01 ± 0.00 | 0.01 ± 0.00 | 0.01 ± 0.00 | 0.01 ± 0.00 | 0.01 ± 0.00 | 0.00 ± 0.00 |
| Heart | 2.74 ± 2.14 | 2.14 ± 0.34 | 2.08 ± 0.32 | 2.08 ± 0.10 | 2.11 ± 0.25 | 2.05 ± 0.31 | 2.25 ± 0.18 |
| Lungs | 1.07 ± 0.21 | 0.57 ± 0.07 | 0.45 ± 0.04 | 0.46 ± 0.07 | 0.37 ± 0.04 | 0.29 ± 0.07 | 0.23 ± 0.01 |
| Liver | 2.99 ± 1.15 | 3.63 ± 0.69 | 2.77 ± 0.51 | 1.59 ± 0.36 | 0.93 ± 0.12 | 0.33 ± 0.05 | 0.21 ± 0.05 |
| Spleen | 1.03 ± 0.31 | 0.88 ± 0.15 | 0.59 ± 0.05 | 0.48 ± 0.03 | 0.31 ± 0.02 | 0.17 ± 0.02 | 0.16 ± 0.03 |
| Adrenal glands | 1.65 ± 0.23 | 1.60 ± 0.33 | 1.80 ± 0.29 | 1.74 ± 0.31 | 1.29 ± 0.38 | 1.30 ± 0.38 | 1.65 ± 0.11 |
| Kidneys | 8.00 ± 0.62 | 8.50 ± 1.92 | 5.09 ± 0.69 | 4.17 ± 0.58 | 3.92 ± 0.51 | 3.02 ± 0.40 | 2.98 ± 0.16 |
| Intestine | 2.28 ± 0.31 | 5.65 ± 1.51 | 8.42 ± 2.25 | 15.58 ± 8.20 | 14.61 ± 7.86 | 10.97 ± 2.29 | 14.39 ± 6.43 |
| Muscle | 0.25 ± 0.03 | 0.18 ± 0.04 | 0.23 ± 0.08 | 0.30 ± 0.02 | 0.22 ± 0.05 | 0.22 ± 0.04 | 0.18 ± 0.05 |

TABLE 16

Biodistribution in rats of the complex [$^{99m}$Tc(N) (PNP5) (ISOET)]$^+$ (% dose/g)

| Organ | 10 min | 2 min | 10 min | 20 min | 30 min | 60 min | 120 min. |
|---|---|---|---|---|---|---|---|
| Blood | 0.93 ± 0.20 | 0.14 ± 0.02 | 0.04 ± 0.01 | 0.02 ± 0.00 | 0.02 ± 0.00 | 0.02 ± 0.00 | 0.01 ± 0.00 |
| Submax. glands | 0.92 ± 0.34 | 0.95 ± 0.21 | 1.40 ± 0.31 | 1.85 ± 0.52 | 1.51 ± 0.07 | 1.79 ± 0.17 | 1.38 ± 0.21 |
| Brain | 0.10 ± 0.02 | 0.02 ± 0.00 | 0.02 ± 0.01 | 0.01 ± 0.01 | 0.01 ± 0.00 | 0.00 ± 0.00 | 0.01 ± 0.01 |
| Heart | 3.35 ± 0.51 | 2.33 ± 0.17 | 2.91 ± 0.36 | 2.86 ± 0.07 | 2.47 ± 0.49 | 2.74 ± 0.19 | 2.44 ± 0.05 |
| Lungs | 2.44 ± 1.06 | 0.74 ± 0.16 | 0.73 ± 0.29 | 0.50 ± 0.09 | 0.45 ± 0.04 | 0.35 ± 0.03 | 0.22 ± 0.03 |
| Liver | 0.95 ± 0.54 | 2.79 ± 0.14 | 1.54 ± 0.10 | 1.09 ± 0.12 | 1.06 ± 0.14 | 0.43 ± 0.15 | 0.23 ± 0.01 |

TABLE 16-continued

Biodistribution in rats of the complex [$^{99m}$Tc(N) (PNP5) (ISOET)]$^+$ (% dose/g)

| Organ | 10 min | 2 min | 10 min | 20 min | 30 min | 60 min | 120 min. |
|---|---|---|---|---|---|---|---|
| Spleen | 1.16 ± 0.20 | 1.11 ± 0.14 | 1.28 ± 0.16 | 1.20 ± 0.23 | 0.35 ± 0.08 | 0.73 ± 0.18 | 0.41 ± 0.13 |
| Adrenal glands | 2.22 ± 0.66 | 2.24 ± 0.15 | 2.70 ± 0.42 | 2.70 ± 0.56 | 2.72 ± 0.35 | 2.23 ± 0.42 | 2.98 ± 0.45 |
| Kidneys | 5.40 ± 1.18 | 7.19 ± 0.40 | 5.98 ± 1.35 | 5.31 ± 0.25 | 5.28 ± 0.41 | 5.12 ± 0.35 | 4.50 ± 0.39 |
| Intestine | 3.70 ± 1.58 | 3.68 ± 0.67 | 7.12 ± 2.04 | 7.44 ± 2.27 | 8.36 ± 0.32 | 8.29 ± 0.61 | 8.00 ± 0.75 |
| Muscle | 0.13 ± 0.01 | 0.16 ± 0.04 | 0.22 ± 0.00 | 0.20 ± 0.01 | 0.13 ± 0.03 | 0.15 ± 0.08 | 0.19 ± 0.05 |

TABLE 17

Biodistribution in rats of the complex [$^{99m}$Tc(N) (PNP5) (BOET)]$^+$ (% dose/g)

| Organ | 0 min | 2 min | 10 min | 20 min | 30 min | 60 min | 120 min. |
|---|---|---|---|---|---|---|---|
| Blood | 0.38 ± 0.15 | 0.10 ± 0.05 | 0.03 ± 0.01 | 0.02 ± 0.00 | 0.02 ± 0.00 | 0.01 ± 0.00 | 0.01 ± 0.00 |
| Submax. glands | 1.28 ± 0.25 | 1.21 ± 0.21 | 1.15 ± 0.04 | 0.94 ± 0.13 | 1.38 ± 0.17 | 1.24 ± 0.12 | 1.17 ± 0.14 |
| Brain | 0.17 ± 0.05 | 0.02 ± 0.00 | 0.01 ± 0.00 | 0.01 ± 0.00 | 0.01 ± 0.00 | 0.00 ± 0.00 | 0.00 ± 0.00 |
| Heart | 3.59 ± 0.78 | 2.89 ± 0.28 | 2.68 ± 0.21 | 2.63 ± 0.21 | 2.56 ± 0.26 | 2.69 ± 0.19 | 2.67 ± 0.45 |
| Lungs | 0.84 ± 0.27 | 0.61 ± 0.21 | 0.54 ± 0.12 | 0.53 ± 0.03 | 0.36 ± 0.03 | 0.40 ± 0.06 | 0.20 ± 0.04 |
| Liver | 3.87 ± 0.19 | 2.44 ± 0.65 | 1.45 ± 0.13 | 1.02 ± 0.27 | 1.11 ± 0.49 | 0.47 ± 0.09 | 0.22 ± 0.06 |
| Spleen | 1.25 ± 0.48 | 1.42 ± 0.09 | 1.09 ± 0.11 | 0.93 ± 0.11 | 0.70 ± 0.05 | 0.55 ± 0.02 | 0.30 ± 0.11 |
| Adrenal glands | 2.59 ± 0.73 | 2.31 ± 0.17 | 2.87 ± 0.16 | 2.55 ± 0.32 | 2.69 ± 0.41 | 2.54 ± 0.23 | 2.84 ± 1.00 |
| Kidneys | 7.59 ± 1.24 | 8.87 ± 1.24 | 7.62 ± 2.32 | 6.94 ± 0.18 | 5.34 ± 0.28 | 5.28 ± 0.58 | 5.06 ± 1.49 |
| Intestine | 4.11 ± 0.46 | 5.63 ± 0.93 | 6.14 ± 2.07 | 8.46 ± 1.55 | 12.02 ± 0.69 | 8.70 ± 4.94 | 5.89 ± 4.35 |
| Muscle | 0.10 ± 0.04 | 0.09 ± 0.01 | 0.19 ± 0.06 | 0.10 ± 0.01 | 0.16 ± 0.12 | 0.14 ± 0.01 | 0.12 ± 0.04 |

TABLE 18

Biodistribution in rats of the complex [$^{99m}$Tc(N) (PNP5) (OBODC)]$^+$ (% dose/g)

| Organ | 0 min | 2 min | 10 min | 20 min | 30 min | 60 min | 120 min. |
|---|---|---|---|---|---|---|---|
| Blood | 1.42 ± 0.76 | 0.17 ± 0.01 | 0.06 ± 0.02 | 0.03 ± 0.01 | 0.05 ± 0.03 | 0.02 ± 0.00 | 0.02 ± 0.01 |
| Submax. glands | 1.17 ± 0.21 | 1.26 ± 0.33 | 1.27 ± 0.20 | 1.03 ± 0.27 | 1.08 ± 0.24 | 1.30 ± 0.19 | 1.36 ± 0.12 |
| Brain | 0.18 ± 0.07 | 0.03 ± 0.00 | 0.03 ± 0.00 | 0.03 ± 0.01 | 0.02 ± 0.01 | 0.01 ± 0.00 | 0.01 ± 0.00 |
| Heart | 2.26 ± 0.82 | 1.241 ± 0.14 | 1.39 ± 0.30 | 1.18 ± 0.18 | 1.05 ± 0.19 | 1.10 ± 0.11 | 1.29 ± 0.16 |
| Lungs | 3.87 ± 1.82 | 1.25 ± 0.42 | 1.10 ± 0.21 | 0.80 ± 0.16 | 0.60 ± 0.08 | 0.48 ± 0.02 | 0.33 ± 0.05 |
| Liver | 3.59 ± 1.82 | 5.94 ± 1.80 | 7.71 ± 1.05 | 6.55 ± 1.88 | 4.66 ± 0.56 | 3.55 ± 0.64 | 2.55 ± 0.69 |
| Spleen | 1.68 ± 0.35 | 3.85 ± 0.26 | 4.00 ± 0.90 | 3.13 ± 0.78 | 2.43 ± 0.23 | 2.64 ± 0.29 | 2.02 ± 0.50 |
| Adrenal glands | 2.60 ± 0.10 | 3.49 ± 1.04 | 4.48 ± 1.75 | 3.19 ± 0.15 | 3.08 ± 0.21 | 3.49 ± 0.16 | 3.47 ± 0.83 |
| Kidneys | 5.56 ± 1.51 | 9.57 ± 1.93 | 9.80 ± 2.06 | 8.18 ± 1.84 | 7.52 ± 1.16 | 6.60 ± 1.29 | 8.83 ± 1.19 |
| Intestine | 2.91 ± 0.73 | 3.54 ± 0.75 | 6.21 ± 0.16 | 8.54 ± 1.88 | 7.75 ± 2.71 | 8.37 ± 3.09 | 9.70 ± 2.51 |
| Muscle | 0.06 ± 0.07 | 0.17 ± 0.07 | 0.16 ± 0.05 | 0.09 ± 0.02 | 0.11 ± 0.01 | 0.12 ± 0.00 | 0.14 ± 0.01 |

TABLE 19

Biodistribution in rats of ($^{99m}$Tc) (MIBI)$^+$ complex (% ID/g)

| Organ | 0 min | 2 min | 10 min | 20 min | 30 min | 60 min | 120 min |
|---|---|---|---|---|---|---|---|
| Blood | 0.34 ± 0.07 | 0.11 ± 0.01 | 0.07 ± 0.01 | 0.05 ± 0.01 | 0.05 ± 0.01 | 0.03 ± 0.00 | 0.02 ± 0.00 |
| Submaxillary glands | 1.43 ± 0.41 | 1.01 ± 0.23 | 1.12 ± 0.12 | 1.07 ± 0.04 | 1.08 ± 0.09 | 1.17 ± 0.05 | 1.19 ± 0.05 |
| Brain | 0.26 ± 0.01 | 0.04 ± 0.01 | 0.05 ± 0.01 | 0.04 ± 0.01 | 0.04 ± 0.02 | 0.04 ± 0.00 | 0.03 ± 0.00 |
| Heart | 3.56 ± 0.22 | 3.25 ± 0.17 | 3.37 ± 0.45 | 3.16 ± 0.22 | 3.70 ± 0.04 | 3.18 ± 0.17 | 3.04 ± 0.14 |
| Lungs | 1.65 ± 0.08 | 1.18 ± 0.13 | 1.36 ± 0.31 | 0.99 ± 0.11 | 0.72 ± 0.06 | 0.47 ± 0.24 | 0.47 ± 0.06 |
| Liver | 1.36 ± 0.12 | 1.88 ± 0.08 | 2.21 ± 0.27 | 1.98 ± 0.60 | 1.37 ± 0.22 | 1.57 ± 0.11 | 1.02 ± 0.23 |
| Spleen | 2.65 ± 0.26 | 2.76 ± 0.66 | 3.16 ± 0.62 | 2.11 ± 0.18 | 2.89 ± 0.29 | 1.88 ± 0.15 | 1.23 ± 0.18 |
| Adrenal Glands | 2.80 ± 0.17 | 1.60 ± 0.01 | 3.28 ± 0.39 | 3.05 ± 0.04 | 3.49 ± 0.67 | 3.50 ± 0.60 | 2.43 ± 0.13 |
| Kidneys | 9.23 ± 0.62 | 10.12 ± 0.15 | 11.45 ± 1.62 | 8.14 ± 1.30 | 6.46 ± 0.11 | 4.42 ± 0.11 | 3.49 ± 0.05 |
| Intestine | 3.55 ± 0.37 | 3.71 ± 0.01 | 5.40 ± 0.33 | 4.90 ± 0.23 | 5.42 ± 0.05 | 6.49 ± 1.43 | 4.15 ± 1.02 |
| Muscle | 0.24 ± 0.04 | 0.14 ± 0.00 | 0.18 ± 0.01 | 0.15 ± 0.05 | 0.17 ± 0.05 | 0.18 ± 0.01 | 0.28 ± 0.05 |

TABLE 20

Biodistribution in rats of ($^{99m}$Tc) (Tf)$^+$ complex (% ID/g)

| Organ | 0 min | 2 min | 10 min | 20 min | 30 min | 60 min | 120 min |
|---|---|---|---|---|---|---|---|
| Blood | 0.48 ± 0.05 | 0.22 ± 0.01 | 0.05 ± 0.00 | 0.04 ± 0.00 | 0.03 ± 0.00 | 0.04 ± 0.01 | 0.02 ± 0.00 |
| Submaxillary glands | 2.06 ± 0.57 | 1.23 ± 0.09 | 1.10 ± 0.13 | 1.27 ± 0.17 | 0.92 ± 0.00 | 1.53 ± 0.13 | 1.13 ± 0.16 |
| Brain | 0.24 ± 0.11 | 0.04 ± 0.00 | 0.03 ± 0.01 | 0.02 ± 0.00 | 0.02 ± 0.00 | 0.02 ± 0.00 | 0.01 ± 0.00 |
| Heart | 2.79 ± 0.42 | 3.15 ± 0.28 | 2.57 ± 0.35 | 2.74 ± 0.13 | 2.45 ± 0.14 | 2.79 ± 0.52 | 2.65 ± 0.07 |
| Lungs | 1.03 ± 0.22 | 0.85 ± 0.08 | 0.77 ± 0.10 | 0.67 ± 0.10 | 0.67 ± 0.08 | 0.51 ± 0.05 | 0.35 ± 0.01 |
| Liver | 2.09 ± 0.30 | 2.52 ± 0.64 | 1.90 ± 0.20 | 1.26 ± 0.29 | 1.28 ± 0.12 | 0.71 ± 0.06 | 0.58 ± 0.15 |
| Spleen | 1.73 ± 0.03 | 2.08 ± 0.45 | 1.40 ± 0.18 | 1.14 ± 0.24 | 1.45 ± 0.04 | 1.11 ± 0.10 | 0.97 ± 0.02 |
| Adrenal Glands | 1.75 ± 0.09 | 2.38 ± 0.12 | 2.28 ± 0.38 | 2.05 ± 0.25 | 1.81 ± 0.18 | 3.08 ± 0.01 | 2.66 ± 0.18 |
| Kidneys | 4.63 ± 0.68 | 9.73 ± 2.17 | 5.52 ± 1.07 | 5.74 ± 0.72 | 4.36 ± 0.14 | 4.05 ± 0.50 | 3.12 ± 0.50 |
| Intestine | 2.64 ± 0.91 | 5.22 ± 0.69 | 7.70 ± 1.41 | 7.33 ± 1.11 | 10.52 ± 1.70 | 8.88 ± 1.94 | 7.02 ± 0.74 |
| Muscle | 0.16 ± 0.04 | 0.29 ± 0.05 | 0.21 ± 0.05 | 0.25 ± 0.01 | 0.18 ± 0.05 | 0.25 ± 0.04 | 0.28 ± 0.12 |

TABLE 21

Heart accumulation in rats of [$^{99m}$Tc(N)](PNP3, PNP5 or PNP6) (XY)$^+$ (% ID/g)

| $^{99m}$-Tc complex | 0 min | 2 min | 10 min | 20 min | 30 min | 60 min | 120 min |
|---|---|---|---|---|---|---|---|
| [$^{99m}$-Tc(N) (PNP3) (DTC)$^+$] | 1.87 ± 0.30 | 2.17 ± 0.02 | 2.58 ± 0.09 | 2.02 ± 0.09 | 1.67 ± 0.05 | 2.20 ± 0.09 | 2.23 ± 0.19 |
| [$^{99m}$-Tc(N) (PNP3) (DMDC)$^+$] | 2.55 ± 0.26 | 2.41 ± 0.14 | 2.45 ± 0.23 | 2.39 ± 0.22 | 2.17 ± 0.07 | 2.55 ± 0.18 | 2.33 ± 0.26 |
| [$^{99m}$-Tc(N) (PNP3) (DEDC)$^+$] | 2.74 ± 0.10 | 2.55 ± 0.02 | 2.85 ± 0.00 | 2.90 ± 0.09 | 2.26 ± 0.20 | 2.50 ± 0.05 | 2.85 ± 0.05 |
| [$^{99m}$-Tc(N) (PNP3) (DPDC)$^+$] | 2.50 ± 0.23 | 2.09 ± 0.18 | 1.92 ± 0.04 | 1.76 ± 0.20 | 1.50 ± 0.06 | 1.74 ± 0.17 | 1.66 ± 0.16 |
| [$^{99m}$-Tc(N) (PNP3) (NOME)$^+$] | 1.23 ± 0.09 | 1.16 ± 0.06 | 1.13 ± 0.07 | 1.15 ± 0.08 | 1.33 ± 0.10 | 1.31 ± 0.05 | 1.16 ± 0.04 |
| [$^{99m}$-Tc(N) (PNP3) (NOET)$^+$] | 2.93 ± 0.02 | 2.87 ± 0.14 | 2.86 ± 0.40 | 3.11 ± 0.77 | 2.97 ± 0.43 | 2.42 ± 0.19 | 2.78 ± 0.21 |
| [$^{99m}$-Tc(N) (PNP3) (PRONE)$^+$] | 2.21 ± 0.23 | 2.65 ± 0.26 | 2.49 ± 0.09 | 2.45 ± 0.24 | 2.31 ± 0.09 | 2.37 ± 0.18 | 2.41 ± 0.17 |
| [$^{99m}$-Tc(N) (PNP3) (BOET)$^+$] | 3.24 ± 0.78 | 3.14 ± 0.08 | 2.88 ± 0.33 | 3.09 ± 0.19 | 2.89 ± 0.18 | 2.84 ± 0.04 | 3.00 ± 0.24 |
| [$^{99m}$-Tc(N) (PNP3) (POET)$^+$] | 2.62 ± 0.06 | 2.76 ± 0.47 | 2.33 ± 0.33 | 2.46 ± 0.15 | 2.62 ± 0.35 | 2.41 ± 0.32 | 2.71 ± 0.23 |
| [$^{99m}$-Tc(N) (PNP3) (DPODC)$^+$] | 3.08 ± 0.31 | 2.06 ± 0.13 | 2.37 ± 0.33 | 2.49 ± 0.31 | 2.57 ± 0.06 | 2.26 ± 0.06 | 2.45 ± 0.41 |
| [$^{99m}$-Tc(N) (PNP3) (DBODC)$^+$] | 3.57 ± 0.14 | 3.42 ± 0.19 | 3.65 ± 0.56 | 3.32 ± 0.18 | 3.27 ± 0.36 | 3.27 ± 0.62 | 3.00 ± 0.42 |
| [$^{99m}$-Tc(N) (PNP5) (DBODC)$^+$] | 5.01 ± 0.16 | 3.94 ± 0.32 | 3.69 ± 0.29 | 3.63 ± 0.46 | 3.73 ± 0.48 | 3.76 ± 0.39 | 3.31 ± 0.06 |
| [$^{99m}$-Tc(N) (PNP5) (NOME)$^+$] | 2.74 ± 2.14 | 2.14 ± 0.34 | 2.08 ± 0.32 | 2.08 ± 0.10 | 2.11 ± 0.25 | 2.05 ± 0.31 | 2.25 ± 0.18 |
| [$^{99m}$-Tc(N) (PNP5) (ISOET)$^+$] | 3.35 ± 0.51 | 2.33 ± 0.17 | 2.91 ± 0.36 | 2.86 ± 0.07 | 2.47 ± 0.49 | 2.74 ± 0.19 | 2.44 ± 0.05 |
| [$^{99m}$-Tc(N) (PNP5) (BOET)$^+$] | 3.59 ± 0.78 | 2.89 ± 0.28 | 2.68 ± 0.21 | 2.63 ± 0.21 | 2.56 ± 0.26 | 2.69 ± 0.19 | 2.67 ± 0.45 |
| [$^{99m}$-Tc(N) (PNP6) (DBODC)$^+$] | 2.26 ± 0.82 | 1.24 ± 0.14 | 1.39 ± 0.30 | 1.18 ± 0.18 | 1.05 ± 0.19 | 1.10 ± 0.11 | 1.29 ± 0.16 |
| ($^{99m}$-Tc) (MIBI)$^+$ | 3.56 ± 0.22 | 3.25 ± 0.17 | 3.37 ± 0.45 | 3.16 ± 0.22 | 3.70 ± 0.04 | 3.18 ± 0.17 | 3.04 ± 0.14 |
| ($^{99m}$-Tc) (Tf)$^+$ | 2.79 ± 0.42 | 3.15 ± 0.28 | 2.57 ± 0.35 | 2.74 ± 0.13 | 2.45 ± 0.14 | 2.79 ± 0.52 | 2.65 ± 0.07 |

TABLE 22

Heart/lung ratio in biodistribution of [$^{99m}$Tc(N)](PNP3, PNP5 or PNP6) (XY)$^+$ in rats

| $^{99m}$-Tc complex | 0 min | 2 min | 10 min | 20 min | 30 min | 60 min | 120 min |
|---|---|---|---|---|---|---|---|
| [$^{99m}$-Tc(N) (PNP3) (DTC)$^{+1}$] | 1.47 | 2.97 | 4.13 | 4.22 | 4.41 | 12.51 | 8.25 |
| [$^{99m}$-Tc(N) (PNP3) (DMDC)$^+$] | 2.18 | 2.80 | 4.54 | 6.29 | 6.58 | 11.09 | 12.94 |
| [$^{99m}$-Tc(N) (PNP3) (DEDC)$^+$] | 1.62 | 3.01 | 3.08 | 2.99 | 3.86 | 4.70 | 5.61 |
| [$^{99m}$-Tc(N) (PNP3) (DPDC)$^+$] | 3.01 | 3.27 | 4.36 | 4.19 | 5.36 | 5.11 | 6.91 |
| [$^{99m}$-Tc(N) (PNP3) (NOME)$^+$] | 1.86 | 3.22 | 3.77 | 4.42 | 4.75 | 6.24 | 7.25 |
| [$^{99m}$-Tc(N) (PNP3) (NOET)$^+$] | 2.27 | 3.28 | 4.55 | 5.42 | 4.98 | 6.31 | 8.27 |
| [$^{99m}$-Tc(N) (PNP3) (PROME)$^+$] | 2.60 | 3.96 | 4.53 | 5.21 | 5.50 | 6.97 | 10.95 |

TABLE 22-continued

Heart/lung ratio in biodistribution of [$^{99m}$Tc(N)](PNP3, PNP5 or PNP6) (XY)$^+$ in rats

| $^{99m}$Tc complex | 0 min | 2 min | 10 min | 20 min | 30 min | 60 min | 120 min |
|---|---|---|---|---|---|---|---|
| [$^{99m}$Tc(N) (PNP3) (BOET)$^+$] | 3.31 | 3.20 | 4.17 | 5.07 | 6.57 | 7.10 | 13.64 |
| [$^{99m}$Tc(N) (PNP3) (POET)$^+$] | 2.40 | 3.29 | 4.16 | 5.23 | 8.45 | 11.48 | 15.06 |
| [$^{99m}$Tc(N) (PNP3) (DPODC)$^+$] | 2.12 | 3.17 | 3.54 | 5.79 | 6.27 | 8.37 | 12.25 |
| [$^{99m}$Tc(N) (PNP3) (DBODC)$^+$] | 2.32 | 3.39 | 4.74 | 3.95 | 4.74 | 9.60 | 11.10 |
| [$^{99m}$Tc(N) (PNP5) (DBODC)$^+$] | 0.76 | 3.98 | 4.19 | 6.37 | 5.83 | 8.17 | 13.24 |
| [$^{99m}$Tc(N) (PNP5) (NOME)$^+$] | 2.56 | 3.75 | 4.62 | 4.52 | 5.70 | 7.07 | 9.78 |
| [$^{99m}$Tc(N) (PNP5) (ISOET)$^+$] | 1.37 | 3.15 | 3.99 | 5.72 | 5.49 | 7.83 | 11.09 |
| [$^{99m}$Tc(N) (PNP5) (BOET)$^+$] | 4.27 | 4.74 | 4.96 | 4.96 | 7.11 | 6.73 | 13.35 |
| [$^{99m}$Tc(N) (PNP6) (DBODC)$^+$] | 0.58 | 0.99 | 1.26 | 1.48 | 1.75 | 2.29 | 3.91 |
| ($^{99m}$Tc) (MIBI)$^+$ | 2.16 | 2.75 | 2.44 | 3.19 | 5.14 | 6.77 | 6.47 |
| ($^{99m}$Tc) (Tf)$^+$ | 2.71 | 3.71 | 3.34 | 4.09 | 3.66 | 5.47 | 7.57 |

TABLE 23

Heart/liver ratio in biodistribution of [$^{99m}$Tc(N)] (PNP3, PNP5 or PNP6) (XY)$^+$ in rats

| $^{99m}$Tc complex | 0 min | 2 min | 10 min | 20 min | 30 min | 60 min | 120 min |
|---|---|---|---|---|---|---|---|
| [$^{99m}$Tc(N) (PNP3) (DTC)$^+$] | 0.83 | 0.63 | 1.16 | 2.61 | 2.79 | 9.56 | 9.44 |
| [$^{99m}$Tc(N) (PNP3) (DMDC)$^+$] | 0.98 | 0.69 | 2.27 | 3.37 | 3.34 | 14.17 | 25.89 |
| [$^{99m}$Tc(N) (PNP3) (DEDC)$^+$] | 1.53 | 0.69 | 1.73 | 3.13 | 6.59 | 13.37 | 19.81 |
| [$^{99m}$Tc(N) (PNP3) (DPDC)$^+$] | 4.39 | 1.23 | 1.71 | 2.44 | 3.49 | 10.24 | 23.71 |
| [$^{99m}$Tc(N) (PNP3) (NOME)$^+$] | 0.99 | 0.66 | 1.49 | 2.13 | 4.43 | 10.92 | 16.57 |
| [$^{99m}$Tc(N) (PNP3) (NOET)$^+$] | 1.88 | 1.08 | 2.11 | 4.55 | 5.52 | 13.31 | 30.21 |
| [$^{99m}$Tc(N) (PNP3) (PROME)$^+$] | 1.31 | 1.11 | 1.43 | 2.85 | 5.25 | 13.17 | 26.78 |
| [$^{99m}$Tc(N) (PNP3) (BOET)$^+$] | 1.73 | 1.55 | 2.36 | 4.29 | 6.42 | 10.92 | 25.01 |
| [$^{99m}$Tc(N) (PNP3) (POET)$^+$] | 1.59 | 1.35 | 1.52 | 3.62 | 6.39 | 20.08 | 27.01 |
| [$^{99m}$Tc(N) (PNP3) (DPODC)$^+$] | 0.89 | 0.56 | 0.68 | 1.34 | 1.98 | 5.38 | 15.31 |
| [$^{99m}$Tc(N) (PNP3) (DBODC)$^+$] | 2.45 | 1.99 | 2.55 | 3.82 | 7.79 | 20.44 | 25.01 |
| [$^{99m}$Tc(N) (PNP5) (DBODC)$^+$] | 6.11 | 1.48 | 2.29 | 3.78 | 5.18 | 18.8 | 33.1 |
| [$^{99m}$Tc(N) (PNP5) (NOME)$^+$] | 0.92 | 0.58 | 0.75 | 1.33 | 2.26 | 6.21 | 10.71 |
| [$^{99m}$Tc(N) (PNP5) (ISOET)$^+$] | 3.53 | 0.83 | 1.90 | 2.62 | 2.33 | 6.37 | 10.61 |
| [$^{99m}$Tc(N) (PNP5) (BOET)$^+$] | 0.93 | 1.18 | 1.84 | 2.58 | 2.30 | 5.72 | 12.14 |
| [$^{99m}$Tc(N) (PNP6) (DBODC)$^+$] | 0.63 | 0.21 | 0.18 | 0.18 | 0.23 | 0.31 | 0.51 |
| ($^{99m}$Tc) (MIBI)$^+$ | 2.62 | 1.73 | 1.52 | 1.61 | 2.71 | 2.03 | 2.98 |
| ($^{99m}$Tc) (Tf)$^+$ | 1.33 | 1.25 | 1.35 | 2.17 | 1.91 | 3.93 | 4.57 |

EXAMPLE 6

Production of a Kit for Preparing a Pharmaceutical for Diagnostic Imaging (1) The following compositions are placed in a vial 1 and a vial 2, respectively, and freeze-dried:

|  |  | Run 1 | Run 2 |
|---|---|---|---|
| Vial 1 | SDH | 5 mg | 5 mg |
|  | EDTA | 5 mg | 5 mg |
|  | SnCl$_2$•2H$_2$O | 0.1 mg | 0.1 mg |
|  | Phosphate buffer (0.1M) | 1 mL | 1 mL |
| Vial 2 | PNP3 | 1.5 mg | 3.5 mg |
|  | DBODC | 3 mg | 3.5 mg |
|  | γ-Cylodextrin | 7.5 mg | 3.5 mg |

(2) From the freeze-dried compositions described above, a pharmaceutical for diagnostic imaging containing a technetium-99m nitride heterocomplex can be obtained as follows.

In the vial 1 was placed 1 to 2 mL of Na[$^{99m}$TcO$_4$] eluted from a $^{99}$Mo—$^{99m}$Tc generator, and the vial 1 is sufficiently shaken and then allowed to stand for 15 minutes. 1.5 mL of physiological saline is placed in the vial 2 to dissolve the contents, and 1 mL of the resulting solution is placed in the vial 1. After thoroughly mixing, the resulting mixture was heated at about 100° C. for 15 minutes and then allowed to cool at room temperature.

Above both preparations showed no effect on the final yield and the amount of the various substances is not critical.

INDUSTRIAL APPLICABILITY

The present inventive radiopharmaceutical for diagnostic imaging containing a technetium-99m nitride heterocomplex as an active ingredient is markedly accumulated in heart and adrenal glands with high heart/lung and heart/liver ratios, and hence has been proved to be useful as radiopharmaceutical for diagnostic imaging of heart and adrenal glands.

The invention claimed is:

1. A radiopharmaceutical for diagnostic imaging, comprising an ion of technetium-99m nitride heterocomplex, represented by following formula (1):

$$[^{99m}Tc(N)(PNP)(XY)]^+ \quad (1)$$

wherein $^{99m}$Tc is a metastable nuclear isomer of technetium-99m;

N is a nitrogen atom bonded to $^{99m}$Tc;

PNP is a bisphosphinoamine ligand coordinated with $^{99m}$Tc and

XY is a bidentate ligand coordinated with $^{99m}$Tc, wherein the bisphosphinoamine ligand is bis(di(methoxypropyl)phosphinoethyl)ethoxyethylamine and the bidentate ligand is selected from the group consisting of N-ethoxyethyl-N-isopropyl dithiocarbamate, N-methoxyethyl-N-ethyl dithiocarbamate, and -N-diethoxyethyl dithiocarbamate.

2. A kit for preparing a radiopharmaceutical for diagnostic imaging according to claim 1, comprising:
   a first container containing a first composition comprising a nitride nitrogen donor and a reducing agent, and
   a second container containing a second composition comprising a bisphosphinoamine compound PNP and a bidentate ligand XY;
   wherein the bisphosphinoamine compound PNP is bis(di(methoxypropyl)phosphinoethyl)ethoxyethylamine and
   the bidentate ligand XY is selected from the group consisting of N-ethoxyethyl-N-isopropyl dithiocarbamate, N-ethoxyethyl-N-ethyl dithiocarbamate; and N-diethoxyethyl dithiocarbamate.

3. A kit for preparing a radiopharmaceutical for diagnostic imaging according to claim 2, wherein the contents of the first and second containers have been freeze-dried.

4. A kit for preparing a radiopharmaceutical for diagnostic imaging according to claim 2, wherein the nitride nitrogen donor is selected from the group consisting of dithiocarbazic acid, dithiocarbazic acid derivatives, hydrazine and.

5. A kit for preparing a radiopharmaceutical for diagnostic imaging according to claim 2, wherein the reducing agent is selected from the group consisting of stannous chloride, sodium hydrogensulfite, sodium borohydride, tertiary phosphines and tris-(m-sulfonatophenyl)phosphine.

* * * * *